(12) United States Patent
Kwon et al.

(10) Patent No.: US 11,987,611 B2
(45) Date of Patent: May 21, 2024

(54) POLYPEPTIDE AND METHOD OF PRODUCING IMP USING THE SAME

(71) Applicant: CJ CHEILJEDANG CORPORATION, Seoul (KR)

(72) Inventors: Jung Gun Kwon, Gimpo-si (KR); Min Ji Baek, Suwon-si (KR); Ji Hye Lee, Anyang-si (KR); Nara Kwon, Yongin-si (KR); Ju Jeong Kim, Suwon-si (KR); Jin Ah Rho, Suwon-si (KR); Jin Man Cho, Seongnam-si (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 18/154,296

(22) Filed: Jan. 13, 2023

(65) Prior Publication Data

US 2023/0227524 A1 Jul. 20, 2023

Related U.S. Application Data

(60) Division of application No. 17/462,738, filed on Aug. 31, 2021, now Pat. No. 11,584,786, which is a division of application No. 16/425,897, filed on May 29, 2019, now Pat. No. 11,180,754, which is a continuation of application No. 16/346,041, filed as application No. PCT/KR2018/015937 on Dec. 14, 2018, now Pat. No. 11,299,521.

(30) Foreign Application Priority Data

Dec. 15, 2017 (KR) .................. 10-2017-0173505

(51) Int. Cl.
| | |
|---|---|
| C12N 1/21 | (2006.01) |
| C07K 14/34 | (2006.01) |
| C07K 14/705 | (2006.01) |
| C12N 1/20 | (2006.01) |
| C12N 15/11 | (2006.01) |
| C12N 15/77 | (2006.01) |
| C12P 19/32 | (2006.01) |
| C12R 1/15 | (2006.01) |

(52) U.S. Cl.
CPC .......... *C07K 14/705* (2013.01); *C07K 14/34* (2013.01); *C12N 1/205* (2021.05); *C12N 15/11* (2013.01); *C12N 15/77* (2013.01); *C12P 19/32* (2013.01); *C12R 2001/15* (2021.05)

(58) Field of Classification Search
None
See application file for complete search history.

(56) References Cited

U.S. PATENT DOCUMENTS

| | | | |
|---|---|---|---|
| 7,767,626 B2 | 8/2010 | Toriyabe et al. | |
| 9,271,500 B2 | 3/2016 | Takahashi et al. | |
| 9,783,509 B2 | 10/2017 | Alig et al. | |
| 9,802,930 B1 | 10/2017 | Tanabe et al. | |
| 9,924,719 B2 | 3/2018 | Tanabe et al. | |
| 10,039,282 B2 | 8/2018 | Wo et al. | |

FOREIGN PATENT DOCUMENTS

| | | |
|---|---|---|
| EP | 3 608 410 A1 | 2/2020 |
| JP | 2-88570 A | 3/1990 |
| KR | 2003-0042972 A | 6/2003 |
| KR | 10-2007-0060207 A | 6/2007 |
| KR | 10-2007-0060208 A | 6/2007 |
| KR | 10-2010-0109732 A | 10/2010 |
| KR | 10-1744958 B1 | 6/2017 |
| KR | 101916622 | 11/2018 |
| WO | 99/55668 A1 | 11/1999 |
| WO | 2010/100189 A1 | 9/2010 |
| WO | 2013/191113 A1 | 12/2013 |
| WO | 2015/004028 A1 | 1/2015 |
| WO | 2015/091267 A1 | 6/2015 |
| WO | 2016/052247 A1 | 4/2016 |
| WO | 2016/052455 A1 | 4/2016 |

OTHER PUBLICATIONS

Adrio et al., "Genetic improvement of processes yielding microbial products," *FEMS Microbiol Rev* 30:187-214 (2006).
European Nucleotide Archive, AMJ44984, Corynebacterium stationis MFS transporter, 2 pages, Feb. 18, 2016.
GenBank: ASJ19118.1, "transcriptional regulator [Corynebacterium stationis]," (two pages) Jul. 5, 2017.
GenBank Accession No. AB0675, probable multidrug efflux STY1517 [imported] *Salmonella enterica* subsp. enterica serovar Typhi (strain CT18) 2 pages, Nov. 18, 2002.
Ishii et al., "Improved Inosine Production and Derepression of Purine Nucleotide Biosynthetic Enzymes in 8-Azaguanine Resistant Mutants of Bacillus subtilis," Agr. Biol. Chem. 36(9): 1511-1522 (1972).
Kisselev, "Polypeptide Release Factors in Prokaryotes and Eukaryotes: Same Function, Different Structure," *Structure* 10:8-9 (2002).
Ledesma-Amaro et al., "Biotechnological production of feed nucleotides by microbial strain improvement," *Process Biochemistry*, http://dx.doi.org/10.1016/j.procbio.2013.06.025, 8 pages (2013).
MFS transporter [Corynebacterium stationis]—GenBank: AMJ44984. 1, Feb. 16, 2016.
Mori et al., "A novel process of inosine 5'-monophosphate production using overexpressed guanosine/inosine kinase," Appl Microbiol Biotechnol, 48:693-698, 1997, 6 pages.
NCBI Reference Sequence WP_066795119.1, retrieved from https://www.ncbi.nlm.nih.gov/protein/1055045151/ on May 23, 2019.
NCBI Reference Sequence WP_066795121.1, retrieved from https://www.ncbi.nlm.nih.gov/protein/WP066795121.1/ on May 24, 2019.
Parkhill et al., "Complete genome sequence of a multiple drug resistant *Salmonella enterica* serovarTyphi CT18," *Nature* 413:848-852 (2001).

(Continued)

*Primary Examiner* — Michael D Pak
(74) *Attorney, Agent, or Firm* — Seed IP Law Group LLP

(57) ABSTRACT

The present disclosure relates to a novel polypeptide having an activity of exporting 5'-inosine monophosphate, a microorganism comprising the same, a method for preparing 5'-inosine monophosphate using the same, and a method for increasing export of 5'-inosine monophosphate.

10 Claims, No Drawings

Specification includes a Sequence Listing.

(56) References Cited

OTHER PUBLICATIONS

Peifer et al., "Metabolic engineering of the purine biosynthetic pathway in Corynebacterium glutamicum results in increased intracellular pool sizes of IMP and hypoxanthine," Microbial Cell Factories, 11:138, 2012, 14 pages.

Sanchez et al., "Metabolic regulation and overproduction of primary metabolites," *Microbiol Biotechnology* 1(4):283-319 (2008).

UniProt Accession No. A0A0FOLG81 (Multidrug resistance protein 3) created Jun. 24, 2015.

UniProtKB—A0A241TXB3_9CORY, Transcriptional regulator, 4 pages, Oct. 25, 2017.

Whisstock et al., "Prediction of protein function from protein sequence and structure," *Quarterly Reviews of Biophysics* 36(3):307-340 (2003).

Witkowski et al., "Conversion of a β-Ketoacyl Synthase to a Malonyl Decarboxylase by Replacement of the Active-Site Cysteine with Glutamine," *Biochemistry* 38:11643-11650 (1999).

POLYPEPTIDE AND METHOD OF PRODUCING IMP USING THE SAME

CROSS-REFERENCE TO RELATED APPLICATIONS

The present application is a divisional application of U.S. application Ser. No. 17/462,738, filed Aug. 31, 2021, which is a divisional application of U.S. application Ser. No. 16/425,897, filed May 29, 2019, now U.S. Pat. No. 11,180,754, which is a continuation application of U.S. application Ser. No. 16/346,041, filed Apr. 29, 2019, now U.S. Pat. No. 11,299,521, which is a U.S. national phase application of PCT/KR2018/015937, filed Dec. 14, 2018, which claims priority to KR Application No. 10-2017-0173505, filed Dec. 15, 2017. U.S. application Ser. Nos. 16/425,897 and 16/346,041 are herein incorporated by reference in their entirety.

REFERENCE TO AN ELECTRONIC SEQUENCE LISTING

The contents of the electronic sequence listing (200187_440D2_SEQUENCE_LISTING.xml; Size: 213,979 bytes; and Date of Creation: Jan. 11, 2023) is herein incorporated by reference in its entirety.

BACKGROUND

Technical Field

The present disclosure relates to a novel protein variant having an activity of exporting 5'-inosine monophosphate (IMP), a microorganism comprising the same, and a method for preparing IMP and a method for increasing export of IMP using the same.

Description of the Related Art

5'-Inosine monophosphate (hereinafter, IMP), a nucleic acid material, is an intermediate of the nucleic acid metabolism pathway and is used in many fields such as foods, medicines, various medical applications, etc. In particular, IMP is widely used as an additive for food seasonings or foods, along with 5'-guanine monophosphate (hereinafter, GMP). Although IMP itself is known to provide a beef taste, it is known to enhance the flavor of monosodium glutamic acid (MSG) and is thus attracting attention as a taste-enhancing nucleic acid-based seasoning.

Examples of methods for producing IMP include a method of enzymatically degrading ribonucleic acid extracted from yeast cells (Japanese Patent Publication No. 1614/1957), a method for chemically phosphorylating inosine produced by fermentation (Agri. Biol. Chem., 36, 1511, etc.), a method for culturing microorganisms which can directly produce IMP and recovering IMP in the culture broth, etc. Among these, the method most frequently used at present is a method using microorganisms capable of directly producing IMP.

Meanwhile, since enzymes do not always exhibit optimal properties in nature with respect to activity, stability, substrate specificity for optical isomers, etc., required in industrial applications, various attempts have been made to improve enzymes to suit the intended use by modification of their amino acid sequences, etc. Among these, although rational design and site-directed mutagenesis of enzymes have been applied to improve enzyme function, in many cases, these attempts were shown to be disadvantageous in that information on the structure of target enzymes is not sufficient or the structure-function correlation is not clear, thus preventing their effective application. Additionally, a method of improving enzyme activity by attempting the enhancement of enzymes through directed evolution, which is for screening enzymes of desired traits from a library of modified enzymes constructed through random mutagenesis of enzyme genes, was previously reported.

BRIEF SUMMARY

Technical Problem

In order to produce IMP in high yield using the method of directly producing IMP through microbial fermentation, the IMP should be smoothly exported. To accomplish such object, the inventors of the present disclosure have discovered the protein involved in the activity of exporting IMP, and also have made many efforts to increase IMP production. As a result, they have discovered protein variants having the activity of exporting IMP, thereby completing the present disclosure.

Technical Solution

An object of the present disclosure is to provide a protein variant having the activity of exporting IMP.

Another object of the present disclosure is to provide a polynucleotide encoding the protein variant of the present disclosure.

Still another object of the present disclosure is to provide a vector including the polynucleotide of the present disclosure.

Still another object of the present disclosure is to provide a microorganism producing IMP, including the protein variant and vector of the present disclosure.

Still another object of the present disclosure is to provide a method for preparing IMP, including culturing the microorganism of the present disclosure in a medium.

Still another object of the present disclosure is to provide a method for increasing the export of IMP, including enhancing activity of the protein variant of the present disclosure, which has the activity of exporting IMP.

Advantageous Effects of the Invention

IMP can be produced in high yield by culturing a microorganism of the genus *Corynebacterium* producing IMP using the protein variant of the present disclosure, which is capable of exporting IMP.

BEST MODE FOR CARRYING OUT THE INVENTION

The present disclosure will be described in detail as follows. Meanwhile, each of the explanations and exemplary embodiments disclosed herein can be applied to other respective explanations and exemplary embodiments. That is, all of the combinations of various factors disclosed herein belong to the scope of the present disclosure. Additionally, the scope of the present disclosure should not be limited by the specific disclosure provided hereinbelow.

To achieve the above objects, an aspect of the present disclosure provides a protein variant having an activity of exporting IMP.

As used herein, the term "a protein that exports 5'-inosine monophosphate (IMP)" refers to a protein involved in the extracellular export of IMP. For the purpose of the present disclosure, the term may be used interchangeably with a protein having an activity of exporting IMP, an IMP export protein, a protein having an activity of exporting 5'-inosine monophosphate, a 5'-inosine monophosphate-exporting protein, etc.; specifically, the protein may be expressed as ImpE, and more specifically, may be expressed as ImpE1 or ImpE2, but is not limited thereto. Additionally, the protein may be derived from a microorganism of the genus *Corynebacterium*, and specifically from *Corynebacterium stationis*, but the microorganism is not limited thereto.

The protein, for example, may consist of the amino acid sequence represented by SEQ ID NO: 1 or SEQ ID NO: 2, but any sequence having the same activity as the protein can be included without limitation, and one of ordinary skill in the art can obtain sequence information from GenBank of NCBI, a well-known database. Additionally, the protein may include the amino acid sequence of SEQ ID NO: 1 or SEQ ID NO: 2, or an amino acid sequence having a homology or identity to the sequence of SEQ ID NO: 1 or SEQ ID NO: 2 of at least 80%, at least 90%, at least 95%, at least 96%, at least 97%, at least 98%, or at least 99%. Additionally, it is obvious that any protein having an amino acid sequence with deletion, modification, substitution, or addition in part of the sequence can also be included in the scope of the present disclosure, as long as the amino acid sequence has a homology or identity described above and has an effect corresponding to that of the protein.

That is, although described as "a protein having an amino acid sequence of a particular SEQ ID NO" or "a protein consisting of an amino acid sequence of a particular SEQ ID NO" in the present disclosure, the protein may have an activity that is identical or corresponding to that of a protein consisting of an amino acid sequence of the corresponding SEQ ID NO. In such a case, it is obvious that any proteins having an amino acid sequence with deletion, modification, substitution, conservative substitution, or addition in part of the sequence also can be used in the present disclosure. For example, in the case of having the activity that is the same as or corresponding to that of the modified protein, it does not exclude an addition of a sequence upstream or downstream of the amino acid sequence, which does not alter the function of the protein, a mutation that may occur naturally, a silent mutation thereof, or a conservative constitution, and even when the sequence addition or mutation is present, it obviously belongs to the scope of the present disclosure.

As used herein, the term "homology" or "identity" refers to a degree of matching with two given amino acid sequences or nucleotide sequences, and may be expressed as a percentage.

The terms "homology" and "identity" may often be used interchangeably with each other.

The sequence homology or identity of conserved polynucleotide or polypeptide sequences may be determined by standard alignment algorithms and can be used with a default gap penalty established by the program being used. Substantially homologous or identical sequences are generally expected to hybridize under moderate or high stringency, along the entire length or at least about 50%, about 60%, about 70%, about 80%, or about 90% of the entire length of the sequences. Polynucleotides that contain degenerate codons instead of codons in the hybridizing polypeptides are also considered.

Whether any two polynucleotide or polypeptide sequences have a homology, similarity, or identity may be determined using a known computer algorithm such as the "FASTA" program (Pearson et al., (1988) [Proc. Natl. Acad. Sci. USA 85]: 2444: using default parameters in 2444). Alternately, it may be determined using the Needleman-Wunsch algorithm (Needleman and Wunsch, 1970, J. Mol. Biol. 48: 443-453), which is performed in the Needleman program of the EMBOSS package ((EMBOSS: The European Molecular Biology Open Software Suite, Rice et al., 2000, Trends Genet. 16: 276-277) (version 5.0.0 or versions thereafter) (GCG program package (Devereux, J., et al., Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, the homology, similarity, or identity may be determined using BLAST or ClustalW of the National Center for Biotechnology Information (NCBI).

The homology, similarity, or identity of polynucleotide or polypeptide sequences may be determined by comparing sequence information using, for example, the GAP computer program (e.g., Needleman et al., (1970), J Mol Biol. 48: 443) as published (e.g., Smith and Waterman, Adv. Appl. Math (1981) 2:482). In summary, the GAP program defines the homology, similarity, or identity as the value obtained by dividing the number of similarly aligned symbols (i.e., nucleotides or amino acids) into the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to relevance between sequences. Specifically, the protein variant of the present disclosure having the activity of exporting IMP may be one in which at least one amino acid selected from the group consisting of the $164^{th}$ amino acid in the amino acid sequence of SEQ ID NO: 1, the $222^{nd}$ amino acid in the amino acid sequence of SEQ ID NO: 1, the $2^{nd}$ amino acid in the amino acid sequence of SEQ ID NO: 2, and the $64^{th}$ amino acid in the amino acid sequence of SEQ ID NO: 2 is substituted with another amino acid, but is not limited thereto.

For example, in the protein variant having the activity of exporting IMP, the $164^{th}$ amino acid in the amino acid sequence of SEQ ID NO: 1 is substituted with lysine, arginine, asparagine, glycine, threonine, or proline; the $2^{nd}$ amino acid in the amino acid sequence of SEQ ID NO: 2 is substituted with isoleucine, phenylalanine, methionine, glutamic acid, histidine, or asparagine; or the $64^{th}$ amino acid in the amino acid sequence of SEQ ID NO: 2 is substituted with aspartic acid, glutamic acid, asparagine, cysteine, isoleucine, or phenylalanine, but is not limited thereto.

As a specific example, the protein variant having the activity of exporting IMP may be a protein having the amino acid sequence consisting of SEQ ID NO: 141, 142, 145, 147, 149, or 151, a protein having an amino acid sequence encoded by the polynucleotide of SEQ ID NO: 153 or 154, or a protein having an amino acid sequence having a homology thereto of at least 80%, at least 90%, at least 95%, at least 96%, at least 97%, at least 98%, or at least 99%. In addition, it is apparent that a protein having a deletion, modification, substitution, or addition of some sequence may be used as the protein of the present disclosure as long as it is a protein having the amino acid sequence with the homology above and exhibiting an effect corresponding to that of the protein.

Another aspect of the present disclosure provides a polynucleotide encoding the protein variant, or a vector including the polynucleotide.

As used herein, the term "polynucleotide" refers to a polymer of nucleotides which is extended in a long chain by covalent bonds and has a DNA strand or an RNA strand longer than a certain length, and more specifically, refers to a polynucleotide fragment encoding the protein variant.

It is apparent that a polynucleotide, which can be translated by codon degeneracy into a protein consisting of the amino acid sequence of SEQ ID NO: 141, 142, 145, 147, 149, or 151, a protein consisting of an amino acid sequence encoded by the polynucleotide of SEQ ID NO: 153 or 154, or into a protein having a homology thereto, also can be included as the polynucleotide of the present disclosure. For example, the polynucleotide of the present disclosure may be a polynucleotide having a nucleotide sequence of SEQ ID NO: 143, 144, 146, 148, 150, 152, 153, or 154, and more specifically, may be a polynucleotide composed of a nucleotide sequence of SEQ ID NO: 143, 144, 146, 148, 150, 152, 153, or 154. In addition, a polynucleotide sequence, which encodes a protein having the activity of the protein consisting of an amino acid sequence of SEQ ID NO: 141, 142, 145, 147, 149, or 151 or an amino acid sequence encoded by a polynucleotide of SEQ ID NO: 153 or 154 by hybridization under stringent conditions with a probe which can be prepared from known gene sequences, e.g., a complementary sequence to all or part of the nucleotide sequence, may be included without limitation.

The term "stringent conditions" refers to conditions under which specific hybridization between polynucleotides is made possible. Such conditions are specifically described in references (e.g., J. Sambrook et al., supra). For example, the conditions may include performing hybridization between genes having a high homology, a homology of 40% or higher, specifically 90% or higher, more specifically 95% or higher, even more specifically 97% or higher, and most specifically 99% or higher, while not performing hybridization between genes having a homology of lower than the above homologies; or to perform hybridization once, specifically two or three times, under conventional washing conditions for southern hybridization of 60° C., 1×SSC, and 0.1% SDS, specifically at a salt concentration and temperature corresponding to 60° C., 0.1×SSC, and 0.1% SDS, and more specifically 68° C., 0.1×SSC, and 0.1% SDS.

Hybridization requires that two nucleic acids have a complementary sequence, although mismatches between bases may be possible depending on the stringency of the hybridization. The term "complementary" is used to describe the relationship between mutually hybridizable nucleotide bases. For example, with respect to DNA, adenosine is complementary to thymine, and cytosine is complementary to guanine. Accordingly, the present disclosure may also include isolated nucleic acid fragments complementary to the entire sequence as well as substantially similar nucleic acid sequences.

Specifically, polynucleotides having a homology can be detected at a $T_m$ value of 55° C. using hybridization conditions that include a hybridization step and using the conditions described above. Additionally, the Tm value may be 60° C., 63° C., or 65° C., but is not limited thereto and may be appropriately adjusted by an ordinary person skilled in the art according to the intended purpose.

The stringency suitable for the hybridization of polynucleotides depends on the length and complementarity of the polynucleotides and the related variables are well known in the art (see Sambrook et al., supra, 9.50 to 9.51 and 11.7 to 11.8).

As used herein, the term "vector" refers to a DNA construct including the nucleotide sequence of the polynucleotide encoding a target protein, in which the target protein is operably linked to a suitable control sequence so that the target protein can be expressed in an appropriate host. The control sequence may include a promoter capable of initiating transcription, any operator sequence for controlling the transcription, a sequence encoding an appropriate mRNA ribosome-binding domain, and a sequence controlling the termination of transcription and translation. The vector, after being transformed into a suitable host cell, may be replicated or function irrespective of the host genome, or may be integrated into the host genome itself.

The vector used in the present disclosure may not be particularly limited as long as the vector is replicable in the host cell, and it may be constructed using any vector known in the art. Examples of the vector may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used; and as a plasmid vector, those based on pBR, pUC, pBluescriptII, pGEM, pTZ, pCL, pET, etc., may be used. Specifically, pDZ, pACYC177, pACYC184, pCL, pECCG117, pUC19, pBR322, pMW118, pCC1BAC vectors, etc., may be used.

In an embodiment, the polynucleotide encoding the target protein may be replaced with a modified polynucleotide within the chromosome using a vector for the insertion into the chromosome in a cell. The insertion of the polynucleotide into the chromosome may be performed using a known method in the art, for example, by homologous recombination, but is not limited thereto. In particular, a selection marker for confirming the insertion into the chromosome may be further included. The selection marker is used for selection of a transformed cell, i.e., in order to confirm whether the target nucleic acid has been inserted, and markers capable of providing selectable phenotypes such as drug resistance, nutrient requirement, resistance to cytotoxic agents, and expression of surface proteins may be used. Under the circumstances where selective agents are treated, only the cells capable of expressing the selection markers can survive or express other phenotypic traits, and thus the transformed cells can be easily selected.

Still another aspect of the present disclosure provides a microorganism producing IMP, including the protein variant of the present disclosure, the polynucleotide of the present disclosure encoding the protein variant, or the vector of the present disclosure. Specifically, the microorganism including the protein variant and/or a polynucleotide encoding the protein variant may be a microorganism prepared by transformation using a vector containing the polynucleotide encoding the protein variant, but the microorganism is not limited thereto.

As used herein, the term "transformation" refers to a process of introducing a vector including a polynucleotide encoding a target protein into a host cell, thereby enabling the expression of the protein encoded by the polynucleotide in the host cell. For the transformed polynucleotide, it does not matter whether it is inserted into the chromosome of the host cell and located therein or located outside the chromosome, as long as the transformed polynucleotide can be expressed in the host cell. Additionally, the polynucleotide includes DNA and RNA which encode the target protein. The polynucleotide may be inserted in any form as long as it can be introduced into a host cell and expressed therein. For example, the polynucleotide may be introduced into a host cell in the form of an expression cassette, which is a gene construct including all of the essential elements required for self-expression. The expression cassette may conventionally include a promoter operably linked to the polynucleotide, a transcription termination signal, a ribosome-binding domain, and a translation termination signal. The expression cassette may be in the form of a self-replicable expression vector. Additionally, the polynucleotide may be introduced into a host cell as is and operably linked to a sequence essential for its expression in the host cell, but is not limited thereto.

Additionally, as used herein, the term "operably linked" refers to a functional linkage between a promoter sequence, which initiates and mediates the transcription of the polynucleotide encoding the target protein, i.e., a conjugate of the present disclosure, and the above gene sequence.

As used herein, the term "IMP-producing microorganism" refers to a microorganism which is naturally capable of producing IMP; or a microorganism introduced an ability to produce or export IMP to whose parent strain is not naturally capable of producing and/or exporting IMP which is In the present disclosure, the microorganism producing IMP can be used interchangeably with a microorganism having an activity of exporting IMP.

The IMP-producing microorganism is a cell or microorganism which includes a protein variant having an activity of exporting IMP or a polynucleotide encoding the protein variant, or which is transformed with a vector containing the polynucleotide encoding the protein variant, and is thereby capable of expressing the protein variant. For the purposes of the present disclosure, the host cell of the IMP-producing microorganism or microorganism may be any microorganism including the protein variant thus capable of producing IMP. For example, the microorganism may be a microorganism of the genus *Escherichia*, a microorganism of the genus *Serratia*, a microorganism of the genus *Erwinia*, a microorganism of the genus Enterobacteria, a microorganism of the genus *Salmonella*, a microorganism of the genus *Streptomyces*, a microorganism of the genus *Pseudomonas*, a microorganism of the genus *Brevibacterium*, a microorganism of the genus *Corynebacterium*, etc., and specifically, a microorganism of the genus *Corynebacterium*.

As used herein, the term "IMP-producing microorganism of the genus *Corynebacterium*" refers to a microorganism of the genus *Corynebacterium* which is naturally capable of producing IMP or capable of producing IMP by modification. Specifically, as used herein, the microorganism of the genus *Corynebacterium* capable of producing IMP refers to a native strain of the microorganism of the genus *Corynebacterium* capable of producing IMP; or a microorganism of the genus *Corynebacterium* with enhanced abilities to produce IMP prepared by inserting a gene associated with IMP production or by enhancing or attenuating the endogenous gene associated with IMP production. More specifically, in the present disclosure, the microorganism of the genus *Corynebacterium* capable of producing IMP refers to a microorganism of the genus *Corynebacterium* which has improved abilities to produce IMP by including a protein variant having an activity of exporting IMP or a polynucleotide encoding the protein variant, or by being transformed with a vector containing the polynucleotide encoding the protein variant. The "microorganism of the genus *Corynebacterium* with enhanced abilities to produce IMP" refers to a microorganism of the genus *Corynebacterium* with improved abilities to produce IMP compared to that of its parent strain before transformation or that of an unmodified microorganism of the genus *Corynebacterium*. The "unmodified microorganism of the genus *Corynebacterium*" refers to a native type of the microorganism of the genus *Corynebacterium*, a microorganism of the genus *Corynebacterium* which does not contain a protein variant capable of exporting IMP, or a microorganism of the genus *Corynebacterium* which is not transformed with a vector containing a polynucleotide encoding the protein variant capable of exporting IMP.

In an embodiment of the present disclosure, the microorganism of the present disclosure may be a microorganism of the genus *Corynebacterium*, in which the activity of adenylosuccinate synthetase and/or IMP dehydrogenase is further attenuated.

In the present disclosure, "a microorganism of the genus *Corynebacterium*" specifically refers to *Corynebacterium glutamicum*, *Corynebacterium ammoniagenes*, *Brevibacterium lactofermentum*, *Brevibacterium flavum*, *Corynebacterium thermoaminogenes*, *Corynebacterium efficiens*, *Corynebacterium stationis*, etc., but the microorganism is not necessarily limited thereto.

Still another aspect of the present disclosure provides a method for preparing IMP, including culturing the microorganism of the genus *Corynebacterium* in a medium.

Specifically, the method of the present disclosure may additionally include a step of recovering IMP from the microorganism or medium.

In the above method, the cultivation of the microorganism may be performed in a batch process, continuous process, fed-batch process, etc., known in the art, but the cultivation process is not particularly limited thereto. In particular, with respect to the cultivation conditions, the pH of the culture may be adjusted to a suitable pH (e.g., pH 5 to 9, specifically pH 6 to 8, and most specifically with an appropriate basic compound (e.g., sodium hydroxide, potassium hydroxide, or ammonia) or acidic compound (e.g., phosphoric acid or sulfuric acid), and the aerobic condition of the culture may be maintained by introducing oxygen or an oxygen-containing gas mixture to the culture. The cultivation temperature may generally be in the range of 20° C. to 45° C., and specifically 25° C. to 40° C. for about 10 to 160 hours, but the cultivation conditions are not limited thereto. The IMP produced by the above cultivation may be secreted into the culture or may be retained in the cells.

Additionally, examples of the carbon sources to be used in the culture medium may include sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); and organic acids (e.g., acetic acid), but are not limited thereto. These carbon sources may be used alone or in combination, but are not limited thereto. Examples of the nitrogen sources to be used in the culture medium may include nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. These nitrogen sources may be used alone or in combination, but are not limited thereto. Examples of the phosphorus sources to be used in the culture medium may include potassium dihydrogen phosphate, dipotassium hydrogen phosphate, corresponding sodium-containing salts, etc., but are not limited thereto. Additionally, metal salts (e.g., magnesium sulfate or iron sulfate), amino acids, vitamins, etc., which are essential growth-promoting materials, may be contained in the medium.

In the present disclosure, the method for recovering the IMP produced in the step of cultivation may be performed by collecting the IMP from the culture broth using an appropriate method known in the art. For example, methods such as centrifugation, filtration, anion exchange chromatography, crystallization, HPLC, etc., may be used, and the desired IMP can be recovered from a culture or cultured microorganism using an appropriate method known in the art.

Further, the recovery may include a purification process and may be performed using an appropriate method known in the art. Thus, the IMP to be recovered may be in a purified form or a microorganism fermentation broth containing IMP.

Still another aspect of the present disclosure provides a composition for producing IMP, including the protein variant of the present disclosure, which has the activity of exporting IMP, or a polynucleotide encoding the same.

The composition of the present disclosure may further include, without limitation, a constitution capable of operating the polynucleotide. In the composition of the present disclosure, the polynucleotide may be in a form included within a vector to express an operably linked gene in the introduced host cell.

Additionally, the composition may further include any suitable excipients conventionally used in the composition for producing IMP. Such excipients may be, for example, preservatives, humectants, suspending agents, buffers, stabilizing agents, or isotonic agents, but are not limited thereto.

Still another aspect of the present disclosure provides use of the protein of the present disclosure for increasing the production of IMP in the microorganism of the genus *Corynebacterium*.

Still another aspect of the present disclosure provides a method for increasing the export of IMP, including enhancing the activity of the protein variant, which has the activity of exporting IMP, in the microorganism of the genus *Corynebacterium*.

The terms "protein having the activity of exporting IMP", "enhancement", and "microorganism of the genus *Corynebacterium*" are as described above.

Still another aspect of the present disclosure provides use of the protein of the present disclosure for increasing the export of IMP in the microorganism of the genus *Corynebacterium*.

DETAILED DESCRIPTION

Hereinafter, the present disclosure will be described in detail through exemplary embodiments. However, it should be obvious to one of ordinary skill in the art that these exemplary embodiments are provided for the purpose of illustration only and are not intended to limit the scope of the present disclosure.

Example 1

Discovery of IMP Export Proteins

A genomic DNA library of *Corynebacterium stationis* ATCC6872 was prepared for the identification of membrane proteins of *Corynebacterium* involved in the export of IMP. Then, since the wild-type strain of *Corynebacterium* cannot produce IMP, or even if it does produce IMP, it produces only a small amount thereof, a strain called CJI0323, which is capable of producing IMP, derived from the ATCC6872 strain was prepared for the identification of the ability to produce IMP. The CJI0323 strain prepared was subjected to screening of membrane proteins involved in IMP export using the genomic DNA library of the ATCC6872 strain. The specific details of the experiment are as follows.

Example 1-1

Selection of IMP-Producing Strain, CJI0323

The ATCC6872 cells were suspended in a phosphate buffer (pH 7.0) or citrate buffer (pH 5.5) at a concentration of $10^7$ cells/mL to $10^8$ cells/mL to prepare an ATCC6872-derived IMP-producing strain, and the cells were subjected to UV treatment to induce mutation. The resulting cells were washed twice with a 0.85% saline solution, and then diluted and plated on a medium, which was prepared by adding a resistance-providing material at an appropriate concentration to a minimal medium containing 1.7% agar, and colonies were obtained thereafter. Each colony was cultured in a nutrient medium and cultured in a seed medium for 24 hours. After culturing the colonies for 3 to 4 days in a fermentation medium, the colony with the highest abilities to produce IMP accumulated in the culture medium was selected. In the course of preparing a strain capable of producing IMP at high concentration, in order to provide adenine auxotrophy, guanine leakage, lysozyme susceptibility, 3,4-dihydroproline resistance, streptomycin resistance, azetidine carboxylic acid resistance, thiaproline resistance, azaserine resistance, sulfaguanidine resistance, norvaline resistance, and trimethoprim resistance, the procedures above were performed sequentially for each material. As a result, CJI0323, which showed resistance to the above materials and excellent abilities to produce IMP, was finally selected. The degree of resistance between ATCC6872 and CJI0323 was compared and the results are shown in Table 1 below.

TABLE 1

| Characteristics | ATCC6872 | CJI0323 |
| --- | --- | --- |
| Adenine auxotrophy | Non-auxotrophy | Auxotrophy |
| Guanine leakage | Non-auxotrophy | Leaky auxotrophy |
| Lysozyme susceptibility | 80 μg/mL | 8 μg/mL |
| 3,4-Dihydroproline resistance | 1000 μg/mL | 3500 μg/mL |
| Streptomycin resistance | 500 μg/mL | 2000 μg/mL |
| Azetidine carboxylic acid resistance | 5 mg/mL | 30 mg/mL |
| Thiaproline resistance | 10 μg/mL | 100 μg/mL |
| Azaserine resistance | 25 μg/mL | 100 μg/mL |
| Sulfaguanidine resistance | 50 μg/mL | 200 μg/mL |
| Norvaline resistance | 0.2 mg/mL | 2 mg/mL |
| Trimethoprim resistance | 20 μg/mL | 100 μg/mL |

Minimal medium: 2% glucose, 0.3% sodium sulfate, 0.1% $KH_2SO_4$, 0.3% $K_2HPO_4$, 0.3% magnesium sulfate, calcium chloride (10 mg/L), iron sulfate (10 mg/L), zinc sulfate (1 mg/L), manganese chloride (3.6 mg/L), L-cysteine (20 mg/L), calcium pantothenate (10 mg/L), thiamine hydrochloride (5 mg/L), biotin (30 μg/L), adenine (20 mg/L), guanine (20 mg/L), pH 7.3

Nutrient medium: 1% peptone, 1% meat juice, 0.25% sodium chloride, 1% yeast extract, 2% agar, pH 7.2

Seed medium: 1% glucose, 1% peptone, 1% meat juice, 1% yeast extract, 0.25% sodium chloride, adenine (100 mg/L), guanine (100 mg/L), pH 7.5

Fermentation medium: 0.1% sodium glutamate, 1% ammonium chloride, 1.2% magnesium sulfate, 0.01% calcium chloride, iron sulfate (20 mg/L), manganese sulfate (20 mg/L), zinc sulfate (20 mg/L), copper sulfate (5 mg/L), L-cysteine (23 mg/L), alanine (24 mg/L), nicotinic acid (8 mg/L), biotin (45 μg/L), thiamine hydrochloride (5 mg/L), adenine (30 mg/L), 1.9% phosphoric acid (85%), 2.55% glucose, 1.45% fructose Example 1-2

Experiments on Fermentation Titer of CJI0323

The seed medium (2 mL) was dispensed into test tubes (diameter: 18 mm), which were then autoclaved and each inoculated with ATCC6872 and CJI0323. Thereafter, the resultants were shake-cultured at 30° C. for 24 hours and then used as a seed culture solution. The fermentation medium (29 mL) was dispensed into Erlenmeyer flasks (250 mL) for shaking, autoclaved at 121° C. for 15 minutes, and the seed culture solution (2 mL) was inoculated thereto and cultured for 3 days. The culture conditions were set to 170 rpm, 30° C., and a pH of 7.5.

Upon completion of the culture, the amount of IMP produced was measured by HPLC (SHIMAZDU LC20A) and the results of the culture are shown in Table 2 below.

TABLE 2

| Strain | IMP (g/L) |
|---|---|
| ATCC6872 | 0 |
| CJI0323 | 9.52 |

The CJI0323 strain was named as *Corynebacterium stationis* CN01-0323. The strain was deposited under the Budapest Treaty to the Korean Culture Center of Microorganisms (KCCM) on Nov. 7, 2017. In addition, the strain was designated as Accession No. KCCM12151P.

Example 1-3

Discovery of Exporting Proteins

Screening conditions showing growth inhibition of the CJI0323 strain were established by additionally adding IMP to the minimal medium containing 1.7% agar. The plasmids of the genomic library of the ATCC6872 strain were transformed into the CJI0323 strain by electroporation (van der Rest et al. 1999), and those colonies in which the growth inhibition was released under the medium conditions supplemented with an excess amount of IMP were selected. Plasmids were obtained from the selected colonies and analyzed by a sequencing technique. As a result, one kind of membrane protein involved in the release of the growth inhibition was identified under the condition where an excess amount of IMP was added.

The one kind of membrane protein from *Corynebacterium* was identified based on the amino acid sequence of SEQ ID NO: 2 and the nucleotide sequence of SEQ ID NO: 4 (NCBI GenBank: NZ_CP014279, WP_066795121, MFS transporter). The membrane protein is known as the MFS transporter, but its specific function has not been confirmed, and further, its function regarding the IMP export is still unknown. In the present disclosure, the membrane protein was named ImpE2(WT).

Example 2

Identification of impE1 and impE2

Example 2-1

Confirmation of impE1 and impE2

In order to examine the functions of the membrane protein, ImpE2, the gene structure of SEQ ID NO: 4 was confirmed in the NCBI (NCBI GenBank: NZ_CP014279, WP_066795121, MFS transporter). As a result, it was confirmed that the 7 bp starting portion of the ORF of SEQ ID NO: 4 (impE2) overlaps in 7 bp with a different gene (NCBI GenBank: NZ_CP014279, WP_066795119, transcriptional regulator), which is located upstream of impE2. Since the functions of the gene located upstream of impE2 and the protein encoded by the gene have not been confirmed, in the present disclosure, the protein was named ImpE1(WT) (the amino acid sequence of SEQ ID NO: 1 and the nucleotide sequence of SEQ ID NO: 3).

Example 2-2

Preparation of impE1- or impE2-Deficient Vector

In order to confirm whether the deletion of ImpE1 or ImpE2, which are involved in releasing the growth inhibition caused by IMP as identified in Examples 1 and 2-1, in an IMP-producing strain can reduce its IMP-exporting ability, attempts were made to prepare vectors deficient in each of the genes.

The gene fragments for preparing the vectors were obtained by PCR using the genomic DNA of the ATCC6872 strain as a template.

Specifically, the PCR for impE1 was performed using primers of SEQ ID NOS: 5 and 6 and primers of SEQ ID NOS: 7 and 8; and the PCR for impE2 was performed using the primers of SEQ ID NOS: 9 and 10 and primers of SEQ ID NOS: 11 and 12 (Table 3).

TABLE 3

| SEQ ID NO | Primer | Sequence (5' to 3') |
|---|---|---|
| 5 | impE1 kop-1 | GCTCTAGACGAGAAAGCTA AAGCCGGTGA |
| 6 | impE1 kop-2 | GTTTTTAGCTACCATTGTT ACACCCCGTGCAAGTTT |
| 7 | impE1 kop-3 | GCACGGGGTGTAACAATGG TAGCTAAAAACTCCACC |
| 8 | impE1 kop-4 | GCTCTAGAAATAGTTGGGG AAGTCCACTC |
| 9 | impE2 kop-1 | GCTCTAGACTTGGATGACC TGGTGGAAAA |
| 10 | impE2 kop-2 | CTTGGAGAAAATTTCCTAC CATTCCAGTCCTTTCGT |
| 11 | impE2 kop-3 | GGACTGGAATGGTAGGAAA TTTTCTCCAAGGGAAAT |

TABLE 3-continued

| SEQ ID NO | Primer | Sequence (5' to 3') |
|---|---|---|
| 12 | impE2 kop-4 | GGACTAGTGGATTGTGTTGACGCACGATG |
| 13 | impE1E2kop-2 | CTTGGAGAAAATTTCTGTTACACCCCGTGCAAGTTT |
| 14 | impE1E2kop-3 | GCACGGGGTGTAACAGAAATTTTCTCCAAGGGAAAT |

In particular, the primers used were prepared based on information on a gene of *Corynebacterium stationis* (ATCC6872) (NCBI Genbank: NZ_CP014279) registered in NIH GenBank and the nucleotide sequences adjacent thereto.

PCR was performed by initial denaturation at 94° C. for 5 minutes; 25 cycles consisting of denaturation at 94° C. for 30 seconds, annealing at 52° C. for 30 minutes, and polymerization at 72° C. for 1 minute; and final polymerization at 72° C. for 5 minutes.

Overlapping PCR was performed using two fragments of the impE1 gene, which were amplified using the primers of SEQ ID NOS: 5 and 6 and the primers of SEQ ID NOS: 7 and 8, as templates, and as a result, a polynucleotide template (1.8 kbp) was obtained. The obtained gene fragment was cloned into a linearized pDZ vector (Korean Patent No. 10-0924065 and International Patent Publication No. 2008-033001), which was digested with the restriction enzyme (XbaI), and ligated using T4 ligase, and thereby the pDZ-ΔimpE1 vector was prepared. Additionally, overlapping polymerase chain reaction was performed using a fragment of the impE2 gene, amplified using the primers of SEQ ID NOS: 9 and 10, and two fragments of the impE2 gene, amplified using the primers of SEQ ID NOS: 11 and 12, as templates, and as a result, a polynucleotide template (1.7 kbp) was obtained. The obtained gene fragment was digested with restriction enzymes, XbaI and SpeI. The gene fragment was cloned using T4 ligase into a linearized pDZ vector, which had already been digested with the restriction enzyme (XbaI), and thereby the pDZ-_ΔimpE2 vector was prepared.

Example 2-3

Preparation of impE1- and impE2-Integration-Deficient Vectors

Since the impE1 and impE2 genes, which encode proteins involved in releasing the growth inhibition caused by IMP, are overlapped, there is a need to regulate both genes simultaneously. Therefore, attempts were made to prepare a vector in which both impE1 and impE2 are deficient.

For the PCR of impE1 and impE2 genes, primers of SEQ ID NOS: 5 and 13 and primers of SEQ ID NOS: 14 and 12 were used. The primers used were prepared based on information on a gene of *Corynebacterium stationis* (ATCC6872) (NCBI Genbank: NZ_CP014279) registered in NIH GenBank and the nucleotide sequences adjacent thereto. Overlapping PCR was performed using a fragment of the impE1 gene, amplified using the primers of SEQ ID NOS: 5 and 13, and two fragments of the impE2 gene, amplified using the primers of SEQ ID NOS: 14 and 12, as templates, and as a result, a polynucleotide template (2.0 kbp) was obtained. The obtained gene fragments were digested with XbaI and SpeI, respectively. The gene fragments were cloned using T4 ligase into a linearized pDZ vector, which had already been digested with the restriction enzyme (XbaI), and thereby the pDZ-ΔimpE1E2 vector was prepared.

Example 2-4

Preparation of impE1- and impE2-Deficient Strains

The two kinds of plasmids prepared in Example 2-2 and one kind of plasmid prepared in Example 2-3 were each transformed into the CJI0323 strain by electroporation (using the transformation method disclosed in Appl. Microbiol. Biotechnol. (1999) 52: 541 to 545). The strains in which the vector was inserted into the chromosome by recombination of the homologous sequences were selected on a medium containing kanamycin (25 mg/L). The selected primary strains were subjected to a second cross-over. The genetic deficiency in the finally transformed strains was confirmed by performing PCR using the primer pairs of SEQ ID NOS: 5 and 8, SEQ ID NOS: 9 and 12, and SEQ ID NOS: 5 and 12.

The selected strains were named CJI0323_ΔimpE1, CJI0323_ΔimpE2, and CJI0323_ΔimpE1E2. Additionally, the abilities to produce IMP of these strains was evaluated.

The seed medium (2 mL) was dispensed into test tubes (diameter: 18 mm), which were then autoclaved, each inoculated with CJI0323, CJI0323_ΔimpE1, CJI0323_ΔimpE2, and CJI0323_ΔimpE1E2, shake-cultured at 30° C. for 24 hours, and used as seed culture solutions. The fermentation medium (29 mL) was dispensed into Erlenmeyer flasks (250 mL) for shaking and autoclaved at 121° C. for 15 minutes. Then, the seed culture solution (2 mL) was inoculated thereto and the resultant was cultured for 3 days. The culture conditions were set to 170 rpm, 30° C., and a pH of 7.5.

Upon completion of the culture, the amount of IMP produced was measured by HPLC, and the results of the culture are shown in Table 4 below.

TABLE 4

| Strain | IMP (g/L) |
|---|---|
| CJI0323 | 9.52 |
| CJI0323_ΔimpE1 | 1.92 |
| CJI0323_ΔimpE2 | 1.88 |
| CJI0323_ΔimpE1E2 | 1.80 |

The IMP amount accumulated in each strain was compared with that of the parent strain, *Corynebacterium stationis* CJI0323. As a result, it was found that, as shown in Table 4 above, the IMP concentrations of the strains CJI0323_ΔimpE1, CJI0323_ΔimpE2, and CJI0323_ΔimpE1E2 were reduced by about 8 g/L under the same conditions compared to the parent strain, confirming that ImpE1 and ImpE2 are proteins involved in the IMP export.

Example 3

Confirmation of Nucleotide Sequences of impE1 and impE2 of IMP-Producing Strain, CJI0323

In the case of the CJI0323 strain producing IMP at high concentration in Example 1, it is possible that the strain has an improved IMP-exporting ability so as to produce IMP at high concentration. Accordingly, an attempt was made to confirm the presence of any mutation in impE1 and impE2 of the CJI0323 strain.

The chromosomal DNA of the CJI0323 strain was amplified by polymerase chain reaction (hereinafter, "PCR"). Specifically, first, PCR was performed by repeating 28 cycles consisting of denaturation at 94° C. for 1 minute, annealing at 58° C. for 30 seconds, and polymerization at 72° C. for 2 minutes using the chromosomal DNA of the CJI0323 strain as a template along with the primers of SEQ ID NOS: 15 and 16 (Table 5), and thereby a fragment of about 2.8 kbp was amplified.

TABLE 5

| SEQ ID NO | Primer | Sequence (5' to 3') |
|---|---|---|
| 15 | impE1E2 seqF | GAACGGAGTCATCTCCTTTGC |
| 16 | impE1E2 seqR | CCAAACGCTCTGCAAGAAACTG |

Upon analysis of the nucleotide sequence using the same primers, it was confirmed that the 490$^{th}$ nucleotide of the impE1 gene (i.e., g) was substituted with 'a', compared to the nucleotide sequence of the wild-type strain, ATCC6872. This substitution indicates that there was a modification in which the 164$^{th}$ amino acid of the ImpE1 protein (i.e., glutamic acid) was substituted with lysine.

Additionally, it was confirmed that the 4$^{th}$ nucleotide of the impE2 gene (i.e., g) was substituted with 'a' (this means that the 666$^{th}$ nucleotide of the impE1 gene (i.e., g) was substituted with 'a') and the 191$^{st}$ nucleotide of the impE1 gene (i.e., g) was substituted with 'a'. These substitutions indicate that there were modifications in which the 2$^{nd}$ amino acid of the ImpE2 protein (i.e., valine), which corresponds to the 222$^{nd}$ amino acid of the ImpE1 protein, was substituted with isoleucine; and the 64$^{th}$ amino acid of the ImpE2 protein (i.e., glycine) was substituted with glutamic acid.

The impE1 nucleotide of the CJI0323 strain was named impE1_CJI0323 (SEQ ID NO: 143) and the protein thereof was named ImpE1_CJI0323 (SEQ ID NO: 141), whereas the impE2 nucleotide of the CJI0323 strain was named impE2_CJI0323 (SEQ ID NO: 144) and the protein thereof was named ImpE2_CJI0323 (SEQ ID NO: 142).

Example 4

Recovery of Modifications in impE1 and impE2

Example 4-1

Preparation of Vectors for Recovering Modifications in impE1 or impE2

In Example 3, the presence of any modification in impE1 and impE2 of the IMP-producing strain CJI0323 was examined. As a result, it was confirmed that impE1 had one modification and impE2 had two modifications. Since the CJI0323 strain produces IMP at a high concentration, it is highly likely that the modification is one that can improve the ability to export IMP. Accordingly, after recovering the mutated impE1 and impE2 to the native wild-type ImpE without modification, the following experiment was performed to confirm whether each modification actually imparted the IMP-exporting ability.

To prepare a recovery vector, PCR was performed using *Corynebacterium stationis* ATCC6872 as a template.

The impE1impE2 gene fragment amplified using the primers of SEQ ID NOS: 17 and 18 was treated with a restriction enzyme, XbaI, and cloned into the XbaI restriction site on the pDZ vector, and thereby the pDZ-impE1E2 (WT) was prepared.

Example 4-2

Preparation of Vectors with Single Modification in impE1 or impE2

A vector with a single E164K modification in the ImpE1 gene was prepared using the native wild-type strain, *Corynebacterium stationis* ATCC6872, as a template along with the primers of SEQ ID NOS: 19 and 20 and primers of SEQ ID NOS: 21 and 22. Overlapping PCR was performed using an E164K-1 gene fragment amplified using the primers of SEQ ID NOS: 19 and 20 and two E164K-2 gene fragments amplified using the primers of SEQ ID NOS: 21 and 22, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE1(E164K) vector was prepared.

A vector with a single V2I modification in the ImpE2 gene was prepared using the ATCC6872 strain as a template along with the primers of SEQ ID NOS: 19 and 23 and primers of SEQ ID NOS: 24 and 22. Overlapping PCR was performed using a V2I-1 gene fragment amplified using the primers of SEQ ID NOS: 19 and 23 and two V2I-2 gene fragments amplified using the primers of SEQ ID NOS: 24 and 22, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE2(V2I) vector was prepared.

A vector with a single G64E modification in the ImpE2 gene was prepared using the ATCC6872 strain as a template along with the primers of SEQ ID NOS: 19 and 25 and primers of SEQ ID NOS: 26 and 22. Overlapping PCR was performed using a G64E-1 gene fragment amplified using the primers of SEQ ID NOS: 19 and 25 and two G64E-2 gene fragments amplified using the primers of SEQ ID NOS: 26 and 22, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE2(G64E) vector was prepared.

TABLE 6

| SEQ ID NO | Primer | Sequence (5' to 3') |
|---|---|---|
| 17 | impE1E2WTF | GCTCTAGAGAACGGAGTCATCTCCTTTGC |
| 18 | impE1E2WTR | GCTCTAGACCAAACGCTCTGCAAGAAACTG |
| 19 | impE1 164K-1 | GCTCTAGACTTGGATGACCTGGTGGAAAA |
| 20 | impE1 164K-2 | CTGGGGCGCGTTGTTTTTCAGGACTGCTCCGAAGACG |

TABLE 6-continued

| SEQ ID NO | Primer | Sequence (5' to 3') |
|---|---|---|
| 21 | impE1 164K-3 | AACAACGCGCCCCAGAATTGG |
| 22 | impE1 164K-4 | GCTCTAGAAATAGTTGGGGAAG TCCACTC |
| 23 | impE2 V2I-2 | TGGAGTTTTTAGCTATCATTCCA GTCCTTTCGTGTAA |
| 24 | impE2 V2I-3 | TAGCTAAAAACTCCACCCCAA |
| 25 | impE2 G64E-2 | CCGAAAATCATCTGCTCCAAAGA GCTCATCAGCATGG |
| 26 | impE2 G64E-3 | GCAGATGATTTTCGGTTCCGC |

Example 4-3

Recovery of impE1, impE2 Modifications and Preparation of Strains with Single Modification The plasmid prepared in Example 4-1 was transformed into the CJI0323 strain by electroporation (using the transformation method disclosed in Appl. Microbiol. Biotechnol. (1999) 52: 541 to 545). The strains in which the vector was inserted into the chromosome by recombination of the homologous sequences were selected on a medium containing kanamycin (25 mg/L). The selected primary strains were subjected to a second cross-over. The recovery of the modification in the finally transformed strains was confirmed by performing PCR using the primer pair of SEQ ID NOS: 15 and 16, followed by nucleotide sequencing analysis. The prepared strain was named CJI0323_impE1E2 (W7).

The three kinds of plasmids prepared in Example 4-2 were each transformed into the CJI0323_impE1E2(W7) strain by electroporation (using the transformation method disclosed in Appl. Microbiol. Biotechnol. (1999) 52: 541 to 545). The strains in which the vector was inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis. The selected strains were named CJI0323_impE1(E164K), CJI0323_impE2(V2I), and CJI0323_impE2(G64E).

The Corynebacterium stationis CJI0323_impE1(E164K), Corynebacterium stationis CJI0323_impE2(V2I), and Corynebacterium stationis CJI0323_impE2(G64E) strains were deposited under the Budapest Treaty to the Korean Culture Center of Microorganisms (KCCM) on Nov. 2, 2018. In addition, the strains were designated with Accession Nos. KCCM12359P, KCCM12360P, and KCCM12361P, respectively.

Example 4-4

Preparation of impE1- and impE2-Integration-Modified Strains

The pDZ-impE2(V2I) and pDZ-impE2(G64E) plasmids prepared in Example 4-2 were transformed into the CJI0323_impE1(E164K) strain by electroporation (using the transformation method disclosed in Appl. Microbiol. Biotechnol. (1999) 52: 541 to 545). The strains in which the vectors were inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis. The prepared strains were named CJI0323_impE1(E164K)_impE2(V2I) and CJI0323_impE1(164K)_impE2(G64E).

The pDZ-impE2(G64E) plasmid was transformed into the CJI0323_impE2(V2I) strain by electroporation (using the transformation method disclosed in Appl. Microbiol. Biotechnol. (1999) 52: 541 to 545). The strains in which the vector was inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis. The selected strain was named CJI0323_impE2(V2I)(G64E).

Example 4-5

Evaluation of Strains with impE1, impE2 Modifications

The seed medium (2 mL) was dispensed into test tubes (diameter: 18 mm), which were then autoclaved, each inoculated with CJI0323_impE1E2(WT), CJI0323_impE1(E164K), CJI0323_impE2(V2I), CJI0323_impE2(G64E), CJI0323_impE1(E164K)_impE2(V2I), CJI0323_impE1(E164K)_impE2(G64E), and CJI0323_impE2(V2I)(G64E), shake-cultured at 30° C. for 24 hours, and used as seed culture solutions. The fermentation medium (29 mL) was dispensed into Erlenmeyer flasks (250 mL) for shaking and autoclaved at 121° C. for 15 minutes. Then, the seed culture solutions (2 mL) were inoculated thereto and the resultants were cultured for 3 days. The culture conditions were set to 170 rpm, 30° C., and a pH of 7.5.

Upon completion of the culture, the amount of IMP produced was measured by HPLC, and the results of the culture are shown in Table 7 below.

TABLE 7

| Strain | IMP (g/L) |
|---|---|
| CJI0323 | 9.52 |
| CJI0323_impE1E2(WT) | 2.32 |
| CJI0323_impE1(E164K) | 2.57 |
| CJI0323_impE2(V2I) | 3.11 |
| CJI0323_impE2(G64E) | 3.27 |
| CJI0323_impE1(E164K)_impE2(V2I) | 4.24 |
| CJI0323_impE1(E164K)_impE2(G64E) | 6.27 |
| CJI0323_impE2(V2I)(G64E) | 7.35 |

As shown above, it was confirmed that with respect to each modification position, one kind of modification, the integration of two kinds of modifications, and the integration of three kinds of modifications were all involved in the IMP export. Accordingly, in a microorganism of the genus Corynebacterium which does not produce IMP or produces only a small amount thereof, the increase in the amount of IMP production due to modifications of the ImpE protein of the present disclosure can be interpreted to be very meaningful.

Example 5

Substitution of Amino Acids in impE1, impE2 Modifications with Another Amino Acids

Example 5-1

Preparation of Vectors for Substitutional Insertion of Amino Acids in impE1, impE2 Modifications To confirm the positional importance of the representative three kinds of modifications (i.e., impE1(E164K), impE2 (V2I), and impE2(G64E)) with enhanced abilities to produce IMP as identified in the results above, a vector for introducing modifications (e.g., a modification of substituting the 164$^{th}$ amino acid in the amino acid sequence of impE1, the 2$^{nd}$ amino acid in the amino acid sequence of impE2, and the 64$^{th}$ amino acid in the amino acid sequence of impE2 with an another amino acid) was prepared.

Firstly, the procedure of preparing the vector for the introduction of the ImpE1(E164K) modification is as follows.

Based on the reported polynucleotide sequences, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 27 and each of SEQ ID NOS: 28 to 45. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 0.7 kbp polynucleotides were obtained. Then, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 46 and each of SEQ ID NOS: 47 to 64. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 0.7 kbp polynucleotides were obtained.

Overlapping PCR was performed using two fragments obtained from the above results as a template, and thereby 18 kinds of 1.4 kbp polynucleotides to be used as templates were obtained. The obtained gene fragments were digested with a restriction enzyme, SpeI, ligated to the linearized pDZ vector, which had already been digested with a restriction enzyme, XbaI, transformed into *E. coli* DH5α, and the transformants were plated on a solid LB medium containing kanamycin (25 mg/L).

The sequence information on the primers used for the preparation of the vector is shown in Table 8 below.

TABLE 8

| SEQ ID NO | Primer | Sequence (5' to 3') |
|---|---|---|
| 27 | SpeI-impE1 164 1F | GGGACTAGTGATTCCGGCCAACTGTCG |
| 28 | impE1 164-R 1R | TGGGGCGCGTTGGCGTTCAGGATGCTC |
| 29 | impE1 164-H 1R | TGGGGCGCGTTGGTGTTCAGGATGCTC |
| 30 | impE1 164-D 1R | TGGGGCGCGTTGATCTTCAGGATGCTC |
| 31 | impE1 164-S 1R | TGGGGCGCGTTGGGATTCAGGATGCTC |
| 32 | impE1 164-T 1R | TGGGGCGCGTTGGGTTTCAGGATGCTC |
| 33 | impE1 164-N 1R | TGGGGCGCGTTGGTTTTCAGGATGCTC |
| 34 | impE1 164-Q 1R | TGGGGCGCGTTGCTGTTCAGGATGCTC |
| 35 | impE1 164-C 1R | TGGGGCGCGTTGGCATTCAGGATGCTC |
| 36 | impE1 164-G 1R | TGGGGCGCGTTGGCCTTCAGGATGCTC |
| 37 | impE1 164-P 1R | TGGGGCGCGTTGCGGTTCAGGATGCTC |
| 38 | impE1 164-A 1R | TGGGGCGCGTTGGGCTTCAGGATGCTC |
| 39 | impE1 164-V 1R | TGGGGCGCGTTGGACTTCAGGATGCTC |
| 40 | impE1 164-I 1R | TGGGGCGCGTTGGATTTCAGGATGCTC |
| 41 | impE1 164-L 1R | TGGGGCGCGTTGCAGTTCAGGATGCTC |
| 42 | impE1 164-M 1R | TGGGGCGCGTTGCATTTCAGGATGCTC |
| 43 | impE1 164-F 1R | TGGGGCGCGTTGGAATTCAGGATGCTC |
| 44 | impE1 164-Y 1R | TGGGGCGCGTTGGTATTCAGGATGCTC |
| 45 | impE1 164-W 1R | TGGGGCGCGTTGCCATTCAGGATGCTC |
| 46 | SpeI-impE1 164 2R | GGGACTAGTCATGAACTTGCCGCGCTC |
| 47 | impE1 164-R 2F | GAGCATCCTGAACGCCAACGCGCCCCA |
| 48 | impE1 164-H 2F | GAGCATCCTGAACACCAACGCGCCCCA |
| 49 | impE1 164-D 2F | GAGCATCCTGAAGATCAACGCGCCCCA |
| 50 | impE1 164-S 2F | GAGCATCCTGAATCCCAACGCGCCCCA |
| 51 | impE1 164-T 2F | GAGCATCCTGAAACCCAACGCGCCCCA |
| 52 | impE1 164-N 2F | GAGCATCCTGAAAACCAACGCGCCCCA |
| 53 | impE1 164-Q 2F | GAGCATCCTGAACAGCAACGCGCCCCA |
| 54 | impE1 164-C 2F | GAGCATCCTGAATGCCAACGCGCCCCA |
| 55 | impE1 164-G 2F | GAGCATCCTGAAGGCCAACGCGCCCCA |
| 56 | impE1 164-P 2F | GAGCATCCTGAACCGCAACGCGCCCCA |
| 57 | impE1 164-A 2F | GAGCATCCTGAAGGCCAACGCGCCCCA |
| 58 | impE1 164-V 2F | GAGCATCCTGAAGTCCAACGCGCCCCA |
| 59 | impE1 164-I 2F | GAGCATCCTGAAATCCAACGCGCCCCA |
| 60 | impE1 164-L 2F | GAGCATCCTGAACTGCAACGCGCCCCA |

TABLE 8-continued

| SEQ ID NO | Primer | Sequence (5' to 3') |
|---|---|---|
| 61 | impE1 164-M 2F | GAGCATCCTGAAATGCAACGCGCCCA |
| 62 | impE1 164-F 2F | GAGCATCCTGAATTCCAACGCGCCCA |
| 63 | impE1 164-Y 2F | GAGCATCCTGAATACCAACGCGCCCA |
| 64 | impE1 164-W 2F | GAGCATCCTGAATGGCAACGCGCCCA |

After selecting by PCR the colonies transformed with the vector into which the target gene was inserted, the plasmids were obtained using a conventionally known plasmid extraction method. The information on the obtained plasmids is shown in Table 9 below.

TABLE 9

| No. | Plasmid |
|---|---|
| 1 | pDZ-impE1 164R |
| 2 | pDZ-impE1 164H |
| 3 | pDZ-impE1 164D |
| 4 | pDZ-impE1 164S |
| 5 | pDZ-impE1 164T |
| 6 | pDZ-impE1 164N |
| 7 | pDZ-impE1 164Q |
| 8 | pDZ-impE1 164C |
| 9 | pDZ-impE1 164G |
| 10 | pDZ-impE1 164P |
| 11 | pDZ-impE1 164A |
| 12 | pDZ-impE1 164V |
| 13 | pDZ-impE1 164I |
| 14 | pDZ-impE1 164L |
| 15 | pDZ-impE1 164M |
| 16 | pDZ-impE1 164F |
| 17 | pDZ-impE1 164Y |
| 18 | pDZ-impE1 164W |

Secondly, the procedure of preparing the vector for the introduction of the ImpE2(V2I) is as follows.

Based on the reported polynucleotide sequences, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 65 and each of SEQ ID NOS: 66 to 83. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 0.7 kbp polynucleotides were obtained. Then, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 84 and each of SEQ ID NOS: 85 to 102. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 0.7 kbp polynucleotides were obtained.

Overlapping PCR was performed using two fragments obtained from the above results as a template, and thereby 18 kinds of 1.4 kbp polynucleotides to be used as templates were obtained. The obtained gene fragments were digested with a restriction enzyme, XbaI, ligated to the linearized pDZ vector, which had already been digested with a restriction enzyme, XbaI, transformed into *E. coli* DH5α, and the transformants were plated on a solid LB medium containing kanamycin (25 mg/L).

The sequence information on the primers used for the preparation of the vector is shown in Table 10 below.

TABLE 10

| SEQ ID NO | Primer | Sequence (5' to 3') |
|---|---|---|
| 65 | XbaI-impE2 2 1F | GGGTCTAGATTGCATGCTGTGCAAGA |
| 66 | impE2 2-R 1R | GGAGTTTTTAGCGCGCATTCCAGTCCT |
| 67 | impE2 2-H 1R | GGAGTTTTTAGCGTGCATTCCAGTCCT |
| 68 | impE2 2-K 1R | GGAGTTTTTAGCCTTCATTCCAGTCCT |
| 69 | impE2 2-D 1R | GGAGTTTTTAGCGTCCATTCCAGTCCT |
| 70 | impE2 2-E 1R | GGAGTTTTTAGCTTCCATTCCAGTCCT |
| 71 | impE2 2-S 1R | GGAGTTTTTAGCGGACATTCCAGTCCT |
| 72 | impE2 2-T 1R | GGAGTTTTTAGCGGTCATTCCAGTCCT |
| 73 | impE2 2-N 1R | GGAGTTTTTAGCGTTCATTCCAGTCCT |
| 74 | impE2 2-Q 1R | GGAGTTTTTAGCCTGCATTCCAGTCCT |
| 75 | impE2 2-C 1R | GGAGTTTTTAGCGCACATTCCAGTCCT |
| 76 | impE2 2-G 1R | GGAGTTTTTAGCGCCCATTCCAGTCCT |
| 77 | impE2 2-P 1R | GGAGTTTTTAGCTGGCATTCCAGTCCT |
| 78 | impE2 2-A 1R | GGAGTTTTTAGCAGCCATTCCAGTCCT |
| 79 | impE2 2-L 1R | GGAGTTTTTAGCCAGCATTCCAGTCCT |
| 80 | impE2 2-M 1R | GGAGTTTTTAGCCATCATTCCAGTCCT |
| 81 | impE2 2-F 1R | GGAGTTTTTAGCGAACATTCCAGTCCT |
| 82 | impE2 2-Y 1R | GGAGTTTTTAGCGTACATTCCAGTCCT |
| 83 | impE2 2-W 1R | GGAGTTTTTAGCCCACATTCCAGTCCT |
| 84 | XbaI-impE2 2 2R | GGGTCTAGATTGCTCGCCCACGCGCA |
| 85 | impE2 2-R 2F | AGGACTGGAATGCGCGCTAAAAACTCC |
| 86 | impE2 2-H 2F | AGGACTGGAATGCACGCTAAAAACTCC |
| 87 | impE2 2-K 2F | AGGACTGGAATGAAGGCTAAAAACTCC |
| 88 | impE2 2-D 2F | AGGACTGGAATGGACGCTAAAAACTCC |
| 89 | impE2 2-E 2F | AGGACTGGAATGGAAGCTAAAAACTCC |
| 90 | impE2 2-S 2F | AGGACTGGAATGTCCGCTAAAAACTCC |
| 91 | impE2 2-T 2F | AGGACTGGAATGACCGCTAAAAACTCC |
| 92 | impE2 2-N 2F | AGGACTGGAATGAACGCTAAAAACTCC |
| 93 | impE2 2-Q 2F | AGGACTGGAATGCAGGCTAAAAACTCC |
| 94 | impE2 2-C 2F | AGGACTGGAATGTGCGCTAAAAACTCC |
| 95 | impE2 2-G 2F | AGGACTGGAATGGGCGCTAAAAACTCC |
| 96 | impE2 2-P 2F | AGGACTGGAATGCCAGCTAAAAACTCC |
| 97 | impE2 2-A 2F | AGGACTGGAATGGCTGCTAAAAACTCC |

TABLE 10-continued

| SEQ ID NO | Primer | Sequence (5' to 3') |
|---|---|---|
| 98 | impE2 2-L 2F | AGGACTGGAATGCTGGCTAAAAACTCC |
| 99 | impE2 2-M 2F | AGGACTGGAATGATGGCTAAAAACTCC |
| 100 | impE2 2-F 2F | AGGACTGGAATGTTCGCTAAAAACTCC |
| 101 | impE2 2-Y 2F | AGGACTGGAATGTACGCTAAAAACTCC |
| 102 | impE2 2-W 2F | AGGACTGGAATGTGGGCTAAAAACTCC |

After selecting by PCR the colonies transformed with the vector into which the target gene was inserted, the plasmids were obtained using a conventionally known plasmid extraction method. The information on the obtained plasmids is shown in Table 11 below.

TABLE 11

| No. | Plasmid |
|---|---|
| 1 | pDZ-impE2 2R |
| 2 | pDZ-impE2 2H |
| 3 | pDZ-impE2 2K |
| 4 | pDZ-impE2 2D |
| 5 | pDZ-impE2 2E |
| 6 | pDZ-impE2 2S |
| 7 | pDZ-impE2 2T |
| 8 | pDZ-impE2 2N |
| 9 | pDZ-impE2 2Q |
| 10 | pDZ-impE2 2C |
| 11 | pDZ-impE2 2G |
| 12 | pDZ-impE2 2P |
| 13 | pDZ-impE2 2A |
| 14 | pDZ-impE2 2L |
| 15 | pDZ-impE2 2M |
| 16 | pDZ-impE2 2F |
| 17 | pDZ-impE2 2Y |
| 18 | pDZ-impE2 2W |

Lastly, the procedure of preparing the vector for the introduction of the ImpE2(G64E) is as follows.

Based on the reported polynucleotide sequences, the chromosomal genes of *Corynebacterium stationis* CJI0323 were isolated, and gene fragments were obtained by performing PCR using the chromosomal DNA of *Corynebacterium stationis* CJI0323 as a template denaturation at 94° C. for 30 seconds, annealing at 55° C. for 30 seconds, and poly along with primer pairs between the primer of SEQ ID NO: 103 and each of SEQ ID NOS: 104 to 121. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 1 kbp polynucleotides were obtained. Then, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 84 and each of SEQ ID NOS: 85 to 102. PCR was performed by initial denaturation at 94° C. for 5 minutes; 20 cycles consisting of polymerization at 72° C. for 1 minute; and final polymerization at 72° C. for 5 minutes. As a result, 18 kinds of 1 kbp polynucleotides were obtained.

Overlapping PCR was performed using two fragments obtained from the above results as a template, and thereby 18 kinds of 2 kbp polynucleotides to be used as templates were obtained. The obtained gene fragments were digested with a restriction enzyme, XbaI, ligated to the linearized pDZ vector, which had already been digested with a restriction enzyme, XbaI, transformed into *E. coli* DH5α, and the transformants were plated on a solid LB medium containing kanamycin (25 mg/L).

The sequence information on the primers used for the preparation of the vector is shown in Table 12 below.

TABLE 12

| SEQ ID NO | Primer | Sequence (5' to 3') |
|---|---|---|
| 103 | XbaI-impE2 64 1F | GGGTCTAGAAAAGAGCTTAAGGCAGCTGCT |
| 104 | impE2 64-R 1R | GAAAATCATCTGGCGCAAAGAGCTCAT |
| 105 | impE2 64-H 1R | GAAAATCATCTGGTGCAAAGAGCTCAT |
| 106 | impE2 64-D 1R | GAAAATCATCTGGTCCAAAGAGCTCAT |
| 107 | impE2 64-K 1R | GAAAATCATCTGCTTCAAAGAGCTCAT |
| 108 | impE2 64-S 1R | GAAAATCATCTGGGACAAAGAGCTCAT |
| 109 | impE2 64-T 1R | GAAAATCATCTGGGTCAAAGAGCTCAT |
| 110 | impE2 64-N 1R | GAAAATCATCTGGTTCAAAGAGCTCAT |
| 111 | impE2 64-Q 1R | GAAAATCATCTGGTGCAAAGAGCTCAT |
| 112 | impE2 64-C 1R | GAAAATCATCTGGGACAAAGAGCTCAT |
| 113 | impE2 64-P 1R | GAAAATCATCTGTGGCAAAGAGCTCAT |
| 114 | impE2 64-A 1R | GAAAATCATCTGAGCCAAAGAGCTCAT |
| 115 | impE2 64-V 1R | GAAAATCATCTGGACCAAAGAGCTCAT |
| 116 | impE2 64-1 1R | GAAAATCATCTGGATCAAAGAGCTCAT |
| 117 | impE2 64-L 1R | GAAAATCATCTGCAGCAAAGAGCTCAT |
| 118 | impE2 64-M 1R | GAAAATCATCTGGATCAAAGAGCTCAT |
| 119 | impE2 64-F 1R | GAAAATCATCTGGAACAAAGAGCTCAT |
| 120 | impE2 64-Y 1R | GAAAATCATCTGGTACAAAGAGCTCAT |
| 121 | impE2 64-W 1R | GAAAATCATCTGCCACAAAGAGCTCAT |
| 122 | XbaI-impE2 64 2R | GGGTCTAGACGGTCAATGAAGTCTCAACGG |
| 123 | impE2 64-R 2F | ATGAGCTCTTTGCGCCAGATGATTTTC |
| 124 | impE2 64-H 2F | ATGAGCTCTTTGCACCAGATGATTTTC |
| 125 | impE2 64-D 2F | ATGAGCTCTTTGGACCAGATGATTTTC |
| 126 | impE2 64-K 2F | ATGAGCTCTTTGAAGCAGATGATTTTC |
| 127 | impE2 64-S 2F | ATGAGCTCTTTGTCCCAGATGATTTTC |
| 128 | impE2 64-T 2F | ATGAGCTCTTTGACCCAGATGATTTTC |
| 129 | impE2 64-N 2F | ATGAGCTCTTTGAACCAGATGATTTTC |
| 130 | impE2 64-Q 2F | ATGAGCTCTTTGCAGCAGATGATTTTC |
| 131 | impE2 64-C 2F | ATGAGCTCTTTGTGCCAGATGATTTTC |

TABLE 12-continued

| SEQ ID NO | Primer | Sequence (5' to 3') |
|---|---|---|
| 132 | impE2 64-P 2F | ATGAGCTCTTTGCCACAGATGATTTTC |
| 133 | impE2 64-A 2F | ATGAGCTCTTTGGCTCAGATGATTTTC |
| 134 | impE2 64-V 2F | ATGAGCTCTTTGGTCCAGATGATTTTC |
| 135 | impE2 64-I 2F | ATGAGCTCTTTGATCCAGATGATTTTC |
| 136 | impE2 64-L 2F | ATGAGCTCTTTGCTGCAGATGATTTTC |
| 137 | impE2 64-M 2F | ATGAGCTCTTTGATGCAGATGATTTTC |
| 138 | impE2 64-F 2F | ATGAGCTCTTTGTTCCAGATGATTTTC |
| 139 | impE2 64-Y 2F | ATGAGCTCTTTGTACCAGATGATTTTC |
| 140 | impE2 64-W 2F | ATGAGCTCTTTGTGGCAGATGATTTTC |

After selecting by PCR the colonies transformed with the vector into which the target gene was inserted, the plasmids were obtained using a conventionally known plasmid extraction method. The information on the obtained plasmids is shown in Table 13 below.

TABLE 13

| No. | Plasmid |
|---|---|
| 1 | pDZ-impE2 64R |
| 2 | pDZ-impE2 64H |
| 3 | pDZ-impE2 64D |
| 4 | pDZ-impE2 64K |
| 5 | pDZ-impE2 64S |
| 6 | pDZ-impE2 64T |
| 7 | pDZ-impE2 64N |
| 8 | pDZ-impE2 64Q |
| 9 | pDZ-impE2 64C |
| 10 | pDZ-impE2 64P |
| 11 | pDZ-impE2 64A |
| 12 | pDZ-impE2 64V |
| 13 | pDZ-impE2 64I |
| 14 | pDZ-impE2 64L |
| 15 | pDZ-impE2 64M |
| 16 | pDZ-impE2 64F |
| 17 | pDZ-impE2 64Y |
| 18 | pDZ-impE2 64W |

Example 5-2

Preparation of Strains where Amino Acids at Positions of Modified Products (ImpE1, ImpE2) are Substituted with Another Amino Acids, and Comparison of Ability to Produce IMP The 54 kinds of plasmids prepared in Example 5-1 were transformed into the CJI0323 strain. The strains in which the vector was inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis. The strain names according to the inserted modifications are shown in Table 14 below.

TABLE 14

| No. | Strain |
|---|---|
| 1 | CJI0323::impE1(E164R) |
| 2 | CJI0323::impE1(E164H) |
| 3 | CJI0323::impE1(E164D) |
| 4 | CJI0323::impE1(E164S) |
| 5 | CJI0323::impE1(E164T) |
| 6 | CJI0323::impE1(E164N) |
| 7 | CJI0323::impE1(E164Q) |
| 8 | CJI0323::impE1(E164C) |
| 9 | CJI0323::impE1(E164G) |
| 10 | CJI0323::impE1(E164P) |
| 11 | CJI0323::impE1(E164A) |
| 12 | CJI0323::impE1(E164V) |
| 13 | CJI0323::impE1(E164I) |
| 14 | CJI0323::impE1(E164L) |
| 15 | CJI0323::impE1(E164M) |
| 16 | CJI0323::impE1(E164F) |
| 17 | CJI0323::impE1(E164Y) |
| 18 | CJI0323::impE1(E164W) |
| 19 | CJI0323::impE2(V2R) |
| 20 | CJI0323::impE2(V2H) |
| 21 | CJI0323::impE2(V2K) |
| 22 | CJI0323::impE2(V2D) |
| 23 | CJI0323::impE2(V2E) |
| 24 | CJI0323::impE2(V2S) |
| 25 | CJI0323::impE2(V2T) |
| 26 | CJI0323::impE2(V2N) |
| 27 | CJI0323::impE2(V2Q) |
| 28 | CJI0323::impE2(V2C) |
| 29 | CJI0323::impE2(V2G) |
| 30 | CJI0323::impE2(V2P) |
| 31 | CJI0323::impE2(V2A) |
| 32 | CJI0323::impE2(V2L) |
| 33 | CJI0323::impE2(V2M) |
| 34 | CJI0323::impE2(V2F) |
| 35 | CJI0323::impE2(V2Y) |
| 36 | CJI0323::impE2(V2W) |
| 37 | CJI0323::impE2(G64R) |
| 38 | CJI0323::impE2(G64H) |
| 39 | CJI0323:impE2(G64D) |
| 40 | CJI0323::impE2(G64K) |
| 41 | CJI0323::impE2(G64S) |
| 42 | CJI0323::impE2(G64T) |
| 43 | CJI0323::impE2(G64N) |
| 44 | CJI0323::impE2(G64Q) |
| 45 | CJI0323::impE2(G64C) |
| 46 | CJI0323::impE2(G64P) |
| 47 | CJI0323::impE2(G64A) |
| 48 | CJI0323::impE2(G64V) |
| 49 | CJI0323::impE2(G64I) |
| 50 | CJI0323:impE2(G64L) |
| 51 | CJI0323::impE2(G64M) |
| 52 | CJI0323::impE2(G64F) |
| 53 | CJI0323:impE2(G64Y) |
| 54 | CJI0323::impE2(G64W) |

The cultivation was performed in the same manner as in Example 1 and the concentration of IMP produced thereof was analyzed (Table 15).

TABLE 15

Concentration (g/L) of IMP production in strains with combined introduction of impE1, impE2 modifications

| | Strain | Average IMP |
|---|---|---|
| Control | CJI0323_impE1E2(WT) | 2.32 |
| 1 | CJI0323::impE1(E164R) | 9.42 |
| 2 | CJI0323::impE1(E164H) | 8.47 |
| 3 | CJI0323::impE1(E164D) | 7.37 |
| 4 | CJI0323::impE1(E164S) | 8.56 |
| 5 | CJI0323::impE1(E164T) | 8.85 |
| 6 | CJI0323::impE1(E164N) | 9.13 |
| 7 | CJI0323::impE1(E164Q) | 7.45 |
| 8 | CJI0323::impE1(E164C) | 7.37 |
| 9 | CJI0323::impE1(E164G) | 9.13 |

TABLE 15-continued

Concentration (g/L) of IMP production in strains with combined introduction of impE1, impE2 modifications

| | Strain | Average IMP |
|---|---|---|
| 10 | CJI0323::impE1(E164P) | 9.43 |
| 11 | CJI0323::impE1(E164A) | 7.44 |
| 12 | CJI0323::impE1(E164V) | 8.18 |
| 13 | CJI0323::impE1(E164I) | 8.09 |
| 14 | CJI0323::impE1(E164L) | 7.85 |
| 15 | CJI0323::impE1(E164M) | 7.39 |
| 16 | CJI0323::impE1(E164F) | 7.56 |
| 17 | CJI0323::impE1(E164Y) | 7.60 |
| 18 | CJI0323::impE1(E164W) | 8.56 |
| 19 | CJI0323::impE2(V2R) | 7.99 |
| 20 | CJI0323::impE2(V2H) | 8.75 |
| 21 | CJI0323::impE2(V2K) | 8.66 |
| 22 | CJI0323::impE2(V2D) | 8.28 |
| 23 | CJI0323::impE2(V2E) | 9.32 |
| 24 | CJI0323::impE2(V2S) | 6.37 |
| 25 | CJI0323::impE2(V2T) | 8.37 |
| 26 | CJI0323::impE2(V2N) | 9.80 |
| 27 | CJI0323::impE2(V2Q) | 7.04 |
| 28 | CJI0323::impE2(V2C) | 7.23 |
| 29 | CJI0323::impE2(V2G) | 7.71 |
| 30 | CJI0323::impE2(V2P) | 7.80 |
| 31 | CJI0323::impE2(V2A) | 6.57 |
| 32 | CJI0323::impE2(V2L) | 6.42 |
| 33 | CJI0323::impE2(V2M) | 9.20 |
| 34 | CJI0323::impE2(V2F) | 9.43 |
| 35 | CJI0323::impE2(V2Y) | 8.37 |
| 36 | CJI0323::impE2(V2W) | 7.22 |
| 37 | CJI0323::impE2(G64R) | 4.42 |
| 38 | CJI0323::impE2(G64H) | 5.14 |
| 39 | CJI0323::impE2(G64D) | 11.53 |
| 40 | CJI0323::impE2(G64K) | 4.8 |
| 41 | CJI0323::impE2(G64S) | 5.7 |
| 42 | CJI0323::impE2(G64T) | 5.52 |
| 43 | CJI0323::impE2(G64N) | 5.9 |
| 44 | CJI0323::impE2(G64Q) | 4.8 |
| 45 | CJI0323::impE2(G64C) | 5.9 |
| 46 | CJI0323::impE2(G64P) | 4.75 |
| 47 | CJI0323::impE2(G64A) | 4.58 |
| 48 | CJI0323::impE2(G64V) | 4.56 |
| 49 | CJI0323::impE2(G64I) | 5.89 |
| 50 | CJI0323::impE2(G64L) | 5.6 |
| 51 | CJI0323::impE2(G64M) | 4.3 |
| 52 | CJI0323::impE2(G64F) | 5.89 |
| 53 | CJI0323::impE2(G64Y) | 4.6 |
| 54 | CJI0323::impE2(G64W) | 4.76 |

As shown above, all of the modified strains showed an increase in the ability to produce IMP compared to each of the control strains, and thus, it was confirmed that the three positions of modification are important sites that have a significant effect on the increase of the ability of the ImpE protein with respect to IMP export.

Example 6

Introduction of impE1, impE2 Modifications Based on Imp-Producing Strains

Example 6-1

Preparation of Strains with impE1, impE2 Modifications Based on Imp-Producing Strains To confirm the effect of introduction of impE1 and impE2 modifications, An IMP-producing strain was prepared in which the activities of adenylosuccinate synthetase and IMP dehydrogenase corresponding to the degradation pathway of IMP in the ATCC6872 strain were attenuated. The initiation codon was changed by changing the first base from 'a' to 't' in each nucleotide sequence of the two genes purA and guaB, which encode the two enzymes. The strain in which the expression of the two genes was attenuated in the ATCC6872 strain was named CJI9088. The pDZ-impE1 (E164K), pDZ-impE2(V2I), and pDZ-impE2(G64E) vectors prepared in Example 4-2 were transformed into the CJI9088 strain by electroporation, and the pDZ-impE2 (G64D) vector prepared in Example 5-1 was transformed into the CJI9088_impE1(E164K)_impE2(V2I) strain by electroporation. The strains in which the vectors were inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis.

The ability of the prepared strains (i.e., CJI9088, CJI9088_impE1(E164K), CJI9088_impE2(V2I), CJI9088_impE2(G64E), and CJI9088_impE1(E164K)_impE2(V2I)(G64D)) to produce IMP was evaluated. Upon completion of the culture, the amount of IMP production was measured by HPLC and the results are shown in Table 16 below.

TABLE 16

| Strain | IMP (g/L) |
|---|---|
| CJI9088 | 0.52 |
| CJI9088_impE1(E164K) | 0.84 |
| CJI9088_impE2(V2I) | 0.93 |
| CJI9088_impE2(G64E) | 1.73 |
| CJI9088_impE1(E164K)_impE2(V2I)(G64D) | 4.30 |

Upon confirming the amount of IMP accumulated in the culture medium, it was confirmed that these strains showed an increase of IMP production by at least 61%, and a maximum increase of 727%, compared to the parent strain, CJI9088. Accordingly, the increase in the amount of IMP production due to modifications of the ImpE protein of the present disclosure can be interpreted to be very meaningful.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microorganism of the genus *Corynebacterium* producing 5′-inosine monophosphate, which comprises a protein variant exporting 5′-inosine monophosphate; the polynucleotide encoding the protein variant; or a vector comprising the polynucleotide encoding the protein variant; wherein, in the amino acid sequence of SEQ ID NO: 2, (i) the 2$^{nd}$ amino acid, (ii) the 64$^{th}$ amino acid, or (iii) the 2$^{nd}$ amino acid and the 64$^{th}$ amino acid are each substituted with another amino acid.

2. The microorganism of the genus *Corynebacterium* according to claim 1, wherein the 2$^{nd}$ amino acid is substituted with an amino acid selected from the group consisting of isoleucine, phenylalanine, methionine, glutamic acid, histidine, and asparagine; (ii) the 64$^{th}$ amino acid is substituted with an amino acid selected from the group consisting of aspartate, glutamic acid, asparagine, cysteine, isoleucine, and phenylalanine; or (iii) the 2$^{nd}$ amino acid and the 64$^{th}$ amino acid are each substituted with an amino acid selected from the group consisting of methionine, glutamic acid, histidine, asparagine, aspartate, cysteine, isoleucine, and phenylalanine.

3. The microorganism of the genus *Corynebacterium* according to claim 1, wherein the microorganism of the genus *Corynebacterium* is *Corynebacterium stationis*.

4. A method for preparing 5′-inosine monophosphate, comprising culturing the microorganism of the genus *Corynebacterium* of claim 1 in a medium; and recovering 5′-inosine monophosphate from the microorganism or medium.

5. The method according to claim 4, wherein the microorganism of the genus *Corynebacterium* is *Corynebacterium stationis*.

6. The microorganism of the genus *Corynebacterium* according to claim 1, further comprising a protein variant in which the 164th amino acid of SEQ ID NO: 1 is substituted with another amino acid; the polynucleotide encoding the protein variant; or a vector comprising the polynucleotide encoding the protein variant.

7. The microorganism of the genus *Corynebacterium* according to claim 6, wherein the 164$^{th}$ amino acid of SEQ ID NO: 1 is substituted with an amino acid selected from the group consisting of lysine, arginine, asparagine, glycine, threonine, and proline.

8. The microorganism of the genus *Corynebacterium* according to claim 6, wherein the microorganism of the genus *Corynebacterium* is *Corynebacterium stationis*.

9. A method for preparing 5′-inosine monophosphate, comprising culturing the microorganism of the genus *Corynebacterium* of claim 6 in a medium; and recovering 5′-inosine monophosphate from the microorganism or medium.

10. The method according to claim 9, wherein the microorganism of the genus *Corynebacterium* is *Corynebacterium stationis*.

\* \* \* \* \*

```
                              SEQUENCE LISTING

Sequence total quantity: 154
SEQ ID NO: 1              moltype = AA   length = 222
FEATURE                   Location/Qualifiers
REGION                    1..222
                          note = ImpE1
source                    1..222
                          mol_type = protein
                          organism = unidentified
SEQUENCE: 1
LHAVQEVNDN EEDSLPGSDL GLREQKRLAT KHRIEDAATR LVDESSFDKV TIEEICEAAG    60
ISRRTFFNYF STKESAVIGA SSEPLTEKQR NDFLNADASN LLQLMVEQIK QHLESSHQSQ   120
AIHDRRQRIF ADPDVAVRAM AFRKERSRET MELIAQRLRE HPEEQRAPEL DPETEAMLLS   180
GFIREATWMA ISRPDRDCAL PVGDRIYRAM ELVKNYTKGL EW                      222

SEQ ID NO: 2              moltype = AA   length = 549
FEATURE                   Location/Qualifiers
REGION                    1..549
                          note = ImpE2
source                    1..549
                          mol_type = protein
                          organism = unidentified
SEQUENCE: 2
MVAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                           549

SEQ ID NO: 3              moltype = DNA   length = 669
FEATURE                   Location/Qualifiers
misc_feature              1..669
                          note = ImpE1
source                    1..669
                          mol_type = other DNA
                          organism = unidentified
SEQUENCE: 3
ttgcatgctg tgcaagaagt taatgacaat gaagaagact ccctccctgg cagtgacctc    60
gggttaaggg agcagaagcg attggcaacc aagcatcgca tcgaagacgc cgcgacacgg   120
ttggttgatg aatcgagctt tgacaaagta acaattgaag aaatttgcga agccgccggg   180
atttcccgac gcacctttttc taattatttc agcacgaaag aaagcgccgt tattggcgcg   240
tcctcggaac cgttgacgga aaagcaacgc aatgacttct tgaatgctga cgccagcaat   300
ctcctgcagc tgatggttga gcagatcaaa caacacttgg agtcttctca ccagagtcaa   360
gcgattcacg accgtcgtca gcgaatcttt gcggatccgg atgtcgcggt acgtgcaatg   420
gcgtttcgca aggaacgctc acgggaaacc atggagctaa tcgctcaacg tcttcgggag   480
catcctgaag aacaacgcgc cccagaattg gatccggaaa cagaggcgat gctgctgagc   540
ggattcattc gcgaagccac ctggatggct atctcacgac ccgatcgtga ttgtgcactg   600
ccagtggggtg accgcatcta tcgcgcgatg gaattggtaa agaattacac gaaaggactg   660
gaatggtag                                                           669

SEQ ID NO: 4              moltype = DNA   length = 1650
FEATURE                   Location/Qualifiers
misc_feature              1..1650
                          note = ImpE2
source                    1..1650
                          mol_type = other DNA
                          organism = unidentified
SEQUENCE: 4
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg ggcagatgat tttcggttcc gctctgccaa ccatcgtcgg cgagctcggc   240
ggcgtggacc agatgagctg ggtaatttca gcatttatgg tcaccatgac cattgctatg   300
ccactagccg gtcagctcgg tgaccgcatg ggccgcaagt gggtctacat ctcaggtatc   360
tccattttcg ttattggctc gacgctcggt ggctttgcca atggcatggg catgctgatc   420
accgacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
```

```
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt tgggtctggc catgatgggc    960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcacggcg   1140
tttgctttgt ggtggatgtc ccagatgacc gttgagactt cattgaccgg tatcggagtt   1200
cgcttcctg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caatatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgaccccc   1560
gtgattggca tgatggtgcc actggccatt gttgcaatgc tgattttgtt cccactgcgc   1620
caagagcgct tgaaggaaac catcgaataa                                     1650

SEQ ID NO: 5              moltype = DNA   length = 29
FEATURE                   Location/Qualifiers
misc_feature              1..29
                          note = Primer impE1 kop-1
source                    1..29
                          mol_type = other DNA
                          organism = synthetic construct
SEQUENCE: 5
gctctagacg agaaagctaa agccggtga                                           29

SEQ ID NO: 6              moltype = DNA   length = 36
FEATURE                   Location/Qualifiers
misc_feature              1..36
                          note = Primer impE1 kop-2
source                    1..36
                          mol_type = other DNA
                          organism = synthetic construct
SEQUENCE: 6
gtttttagct accattgtta cacccgtgc aagttt                                    36

SEQ ID NO: 7              moltype = DNA   length = 36
FEATURE                   Location/Qualifiers
misc_feature              1..36
                          note = Primer impE1 kop-3
source                    1..36
                          mol_type = other DNA
                          organism = synthetic construct
SEQUENCE: 7
gcacggggtg taacaatggt agctaaaaac tccacc                                   36

SEQ ID NO: 8              moltype = DNA   length = 29
FEATURE                   Location/Qualifiers
misc_feature              1..29
                          note = Primer impE1 kop-4
source                    1..29
                          mol_type = other DNA
                          organism = synthetic construct
SEQUENCE: 8
gctctagaaa tagttgggga agtccactc                                           29

SEQ ID NO: 9              moltype = DNA   length = 29
FEATURE                   Location/Qualifiers
misc_feature              1..29
                          note = Primer impE2 kop-1
source                    1..29
                          mol_type = other DNA
                          organism = synthetic construct
SEQUENCE: 9
gctctagact tggatgacct ggtggaaaa                                           29

SEQ ID NO: 10             moltype = DNA   length = 36
FEATURE                   Location/Qualifiers
misc_feature              1..36
                          note = Primer impE2 kop-2
source                    1..36
                          mol_type = other DNA
                          organism = synthetic construct
SEQUENCE: 10
cttggagaaa atttcctacc attccagtcc tttcgt                                   36

SEQ ID NO: 11             moltype = DNA   length = 36
```

```
FEATURE              Location/Qualifiers
misc_feature         1..36
                     note = Primer impE2 kop-3
source               1..36
                     mol_type = other DNA
                     organism = synthetic construct
SEQUENCE: 11
ggactggaat ggtaggaaat tttctccaag ggaaat                                36

SEQ ID NO: 12        moltype = DNA  length = 29
FEATURE              Location/Qualifiers
misc_feature         1..29
                     note = Primer impE2 kop-4
source               1..29
                     mol_type = other DNA
                     organism = synthetic construct
SEQUENCE: 12
ggactagtgg attgtgttga cgcacgatg                                        29

SEQ ID NO: 13        moltype = DNA  length = 36
FEATURE              Location/Qualifiers
misc_feature         1..36
                     note = Primer impE1E2 kop-2
source               1..36
                     mol_type = other DNA
                     organism = synthetic construct
SEQUENCE: 13
cttggagaaa atttctgtta caccccgtgc aagttt                                36

SEQ ID NO: 14        moltype = DNA  length = 36
FEATURE              Location/Qualifiers
misc_feature         1..36
                     note = Primer impE1E2 kop-3
source               1..36
                     mol_type = other DNA
                     organism = synthetic construct
SEQUENCE: 14
gcacggggtg taacagaaat tttctccaag ggaaat                                36

SEQ ID NO: 15        moltype = DNA  length = 21
FEATURE              Location/Qualifiers
misc_feature         1..21
                     note = Primer impE1E2 seqF
source               1..21
                     mol_type = other DNA
                     organism = synthetic construct
SEQUENCE: 15
gaacggagtc atctcctttg c                                                21

SEQ ID NO: 16        moltype = DNA  length = 22
FEATURE              Location/Qualifiers
misc_feature         1..22
                     note = Primer impE1E2 seqR
source               1..22
                     mol_type = other DNA
                     organism = synthetic construct
SEQUENCE: 16
ccaaacgctc tgcaagaaac tg                                               22

SEQ ID NO: 17        moltype = DNA  length = 29
FEATURE              Location/Qualifiers
misc_feature         1..29
                     note = Primer impE1E2 WT F
source               1..29
                     mol_type = other DNA
                     organism = synthetic construct
SEQUENCE: 17
gctctagaga acggagtcat ctcctttgc                                        29

SEQ ID NO: 18        moltype = DNA  length = 30
FEATURE              Location/Qualifiers
misc_feature         1..30
                     note = Primer impE1E2 WT R
source               1..30
                     mol_type = other DNA
                     organism = synthetic construct
SEQUENCE: 18
gctctagacc aaacgctctg caagaaactg                                       30
```

```
SEQ ID NO: 19              moltype = DNA   length = 29
FEATURE                    Location/Qualifiers
misc_feature               1..29
                           note = Primer impE1 164K-1
source                     1..29
                           mol_type = other DNA
                           organism = synthetic construct
SEQUENCE: 19
gctctagact tggatgacct ggtggaaaa                                       29

SEQ ID NO: 20              moltype = DNA   length = 37
FEATURE                    Location/Qualifiers
misc_feature               1..37
                           note = Primer impE1 164K-2
source                     1..37
                           mol_type = other DNA
                           organism = synthetic construct
SEQUENCE: 20
ctggggcgcg ttgtttttca ggatgctccc gaagacg                              37

SEQ ID NO: 21              moltype = DNA   length = 21
FEATURE                    Location/Qualifiers
misc_feature               1..21
                           note = Primer impE1 164K-3
source                     1..21
                           mol_type = other DNA
                           organism = synthetic construct
SEQUENCE: 21
aacaacgcgc cccagaattg g                                               21

SEQ ID NO: 22              moltype = DNA   length = 29
FEATURE                    Location/Qualifiers
misc_feature               1..29
                           note = Primer impE1 164K-4
source                     1..29
                           mol_type = other DNA
                           organism = synthetic construct
SEQUENCE: 22
gctctagaaa tagttgggga agtccactc                                       29

SEQ ID NO: 23              moltype = DNA   length = 37
FEATURE                    Location/Qualifiers
misc_feature               1..37
                           note = Primer impE2 V2I-2
source                     1..37
                           mol_type = other DNA
                           organism = synthetic construct
SEQUENCE: 23
tggagttttt agctatcatt ccagtccttt cgtgtaa                              37

SEQ ID NO: 24              moltype = DNA   length = 21
FEATURE                    Location/Qualifiers
misc_feature               1..21
                           note = Primer impE2 V2I-3
source                     1..21
                           mol_type = other DNA
                           organism = synthetic construct
SEQUENCE: 24
tagctaaaaa ctccacccca a                                               21

SEQ ID NO: 25              moltype = DNA   length = 37
FEATURE                    Location/Qualifiers
misc_feature               1..37
                           note = Primer impE2 G64E-2
source                     1..37
                           mol_type = other DNA
                           organism = synthetic construct
SEQUENCE: 25
ccgaaaatca tctgctccaa agagctcatc agcatgg                              37

SEQ ID NO: 26              moltype = DNA   length = 21
FEATURE                    Location/Qualifiers
misc_feature               1..21
                           note = Primer impE2 G64E-3
source                     1..21
                           mol_type = other DNA
                           organism = synthetic construct
SEQUENCE: 26
gcagatgatt ttcggttccg c                                               21
```

```
SEQ ID NO: 27            moltype = DNA  length = 27
FEATURE                  Location/Qualifiers
misc_feature             1..27
                         note = Primer Spe1-impE1 164 1F
source                   1..27
                         mol_type = other DNA
                         organism = synthetic construct
SEQUENCE: 27
gggactagtg attccggcca actgtcg                                            27

SEQ ID NO: 28            moltype = DNA  length = 27
FEATURE                  Location/Qualifiers
misc_feature             1..27
                         note = Primer impE1 164-R 1R
source                   1..27
                         mol_type = other DNA
                         organism = synthetic construct
SEQUENCE: 28
tggggcgcgt tggcgttcag gatgctc                                            27

SEQ ID NO: 29            moltype = DNA  length = 27
FEATURE                  Location/Qualifiers
misc_feature             1..27
                         note = Primer impE1 164-H 1R
source                   1..27
                         mol_type = other DNA
                         organism = synthetic construct
SEQUENCE: 29
tggggcgcgt tggtgttcag gatgctc                                            27

SEQ ID NO: 30            moltype = DNA  length = 27
FEATURE                  Location/Qualifiers
misc_feature             1..27
                         note = Primer impE1 164-D 1R
source                   1..27
                         mol_type = other DNA
                         organism = synthetic construct
SEQUENCE: 30
tggggcgcgt tgatcttcag gatgctc                                            27

SEQ ID NO: 31            moltype = DNA  length = 27
FEATURE                  Location/Qualifiers
misc_feature             1..27
                         note = Primer impE1 164-S 1R
source                   1..27
                         mol_type = other DNA
                         organism = synthetic construct
SEQUENCE: 31
tggggcgcgt tgggattcag gatgctc                                            27

SEQ ID NO: 32            moltype = DNA  length = 27
FEATURE                  Location/Qualifiers
misc_feature             1..27
                         note = Primer impE1 164-T 1R
source                   1..27
                         mol_type = other DNA
                         organism = synthetic construct
SEQUENCE: 32
tggggcgcgt tgggtttcag gatgctc                                            27

SEQ ID NO: 33            moltype = DNA  length = 27
FEATURE                  Location/Qualifiers
misc_feature             1..27
                         note = Primer impE1 164-N 1R
source                   1..27
                         mol_type = other DNA
                         organism = synthetic construct
SEQUENCE: 33
tggggcgcgt tggttttcag gatgctc                                            27

SEQ ID NO: 34            moltype = DNA  length = 27
FEATURE                  Location/Qualifiers
misc_feature             1..27
                         note = Primer impE1 164-Q 1R
source                   1..27
                         mol_type = other DNA
                         organism = synthetic construct
SEQUENCE: 34
```
tggggcgcgt tgctgttcag gatgctc                                              27

SEQ ID NO: 35          moltype = DNA   length = 27
FEATURE                Location/Qualifiers
misc_feature           1..27
                       note = Primer impE1 164-C 1R
source                 1..27
                       mol_type = other DNA
                       organism = synthetic construct
SEQUENCE: 35
tggggcgcgt tggcattcag gatgctc                                              27

SEQ ID NO: 36          moltype = DNA   length = 27
FEATURE                Location/Qualifiers
misc_feature           1..27
                       note = Primer impE1 164-G 1R
source                 1..27
                       mol_type = other DNA
                       organism = synthetic construct
SEQUENCE: 36
tggggcgcgt tggccttcag gatgctc                                              27

SEQ ID NO: 37          moltype = DNA   length = 27
FEATURE                Location/Qualifiers
misc_feature           1..27
                       note = Primer impE1 164-P 1R
source                 1..27
                       mol_type = other DNA
                       organism = synthetic construct
SEQUENCE: 37
tggggcgcgt tgcggttcag gatgctc                                              27

SEQ ID NO: 38          moltype = DNA   length = 27
FEATURE                Location/Qualifiers
misc_feature           1..27
                       note = Primer impE1 164-A 1R
source                 1..27
                       mol_type = other DNA
                       organism = synthetic construct
SEQUENCE: 38
tggggcgcgt tgggcttcag gatgctc                                              27

SEQ ID NO: 39          moltype = DNA   length = 27
FEATURE                Location/Qualifiers
misc_feature           1..27
                       note = Primer impE1 164-V 1R
source                 1..27
                       mol_type = other DNA
                       organism = synthetic construct
SEQUENCE: 39
tggggcgcgt tggacttcag gatgctc                                              27

SEQ ID NO: 40          moltype = DNA   length = 27
FEATURE                Location/Qualifiers
misc_feature           1..27
                       note = Primer impE1 164-I 1R
source                 1..27
                       mol_type = other DNA
                       organism = synthetic construct
SEQUENCE: 40
tggggcgcgt tggatttcag gatgctc                                              27

SEQ ID NO: 41          moltype = DNA   length = 27
FEATURE                Location/Qualifiers
misc_feature           1..27
                       note = Primer impE1 164-L 1R
source                 1..27
                       mol_type = other DNA
                       organism = synthetic construct
SEQUENCE: 41
tggggcgcgt tgcagttcag gatgctc                                              27

SEQ ID NO: 42          moltype = DNA   length = 27
FEATURE                Location/Qualifiers
misc_feature           1..27
                       note = Primer impE1 164-M 1R
source                 1..27
                       mol_type = other DNA
                       organism = synthetic construct

```
SEQUENCE: 42
tggggcgcgt tgcatttcag gatgctc                                              27

SEQ ID NO: 43           moltype = DNA   length = 27
FEATURE                 Location/Qualifiers
misc_feature            1..27
                        note = Primer impE1 164-F 1R
source                  1..27
                        mol_type = other DNA
                        organism = synthetic construct
SEQUENCE: 43
tggggcgcgt tggaattcag gatgctc                                              27

SEQ ID NO: 44           moltype = DNA   length = 27
FEATURE                 Location/Qualifiers
misc_feature            1..27
                        note = Primer impE1 164-Y 1R
source                  1..27
                        mol_type = other DNA
                        organism = synthetic construct
SEQUENCE: 44
tggggcgcgt tggtattcag gatgctc                                              27

SEQ ID NO: 45           moltype = DNA   length = 27
FEATURE                 Location/Qualifiers
misc_feature            1..27
                        note = Primer impE1 164-W 1R
source                  1..27
                        mol_type = other DNA
                        organism = synthetic construct
SEQUENCE: 45
tggggcgcgt tgccattcag gatgctc                                              27

SEQ ID NO: 46           moltype = DNA   length = 27
FEATURE                 Location/Qualifiers
misc_feature            1..27
                        note = Primer Spe1-impE1 164 2R
source                  1..27
                        mol_type = other DNA
                        organism = synthetic construct
SEQUENCE: 46
gggactagtc atgaacttgc cgcgctc                                              27

SEQ ID NO: 47           moltype = DNA   length = 27
FEATURE                 Location/Qualifiers
misc_feature            1..27
                        note = Primer impE1 164-R 2F
source                  1..27
                        mol_type = other DNA
                        organism = synthetic construct
SEQUENCE: 47
gagcatcctg aacgccaacg cgcccca                                              27

SEQ ID NO: 48           moltype = DNA   length = 27
FEATURE                 Location/Qualifiers
misc_feature            1..27
                        note = Primer impE1 164-H 2F
source                  1..27
                        mol_type = other DNA
                        organism = synthetic construct
SEQUENCE: 48
gagcatcctg aacaccaacg cgcccca                                              27

SEQ ID NO: 49           moltype = DNA   length = 27
FEATURE                 Location/Qualifiers
misc_feature            1..27
                        note = Primer impE1 164-D 2F
source                  1..27
                        mol_type = other DNA
                        organism = synthetic construct
SEQUENCE: 49
gagcatcctg aagatcaacg cgcccca                                              27

SEQ ID NO: 50           moltype = DNA   length = 27
FEATURE                 Location/Qualifiers
misc_feature            1..27
                        note = Primer impE1 164-S 2F
source                  1..27
                        mol_type = other DNA
```

```
                        organism = synthetic construct
SEQUENCE: 50
gagcatcctg aatcccaacg cgcccca                                              27

SEQ ID NO: 51           moltype = DNA   length = 27
FEATURE                 Location/Qualifiers
misc_feature            1..27
                        note = Primer impE1 164-T 2F
source                  1..27
                        mol_type = other DNA
                        organism = synthetic construct
SEQUENCE: 51
gagcatcctg aaacccaacg cgcccca                                              27

SEQ ID NO: 52           moltype = DNA   length = 27
FEATURE                 Location/Qualifiers
misc_feature            1..27
                        note = Primer impE1 164-N 2F
source                  1..27
                        mol_type = other DNA
                        organism = synthetic construct
SEQUENCE: 52
gagcatcctg aaaaccaacg cgcccca                                              27

SEQ ID NO: 53           moltype = DNA   length = 27
FEATURE                 Location/Qualifiers
misc_feature            1..27
                        note = Primer impE1 164-Q 2F
source                  1..27
                        mol_type = other DNA
                        organism = synthetic construct
SEQUENCE: 53
gagcatcctg aacagcaacg cgcccca                                              27

SEQ ID NO: 54           moltype = DNA   length = 27
FEATURE                 Location/Qualifiers
misc_feature            1..27
                        note = Primer impE1 164-C 2F
source                  1..27
                        mol_type = other DNA
                        organism = synthetic construct
SEQUENCE: 54
gagcatcctg aatgccaacg cgcccca                                              27

SEQ ID NO: 55           moltype = DNA   length = 27
FEATURE                 Location/Qualifiers
misc_feature            1..27
                        note = Primer impE1 164-G 2F
source                  1..27
                        mol_type = other DNA
                        organism = synthetic construct
SEQUENCE: 55
gagcatcctg aaggccaacg cgcccca                                              27

SEQ ID NO: 56           moltype = DNA   length = 27
FEATURE                 Location/Qualifiers
misc_feature            1..27
                        note = Primer impE1 164-P 2F
source                  1..27
                        mol_type = other DNA
                        organism = synthetic construct
SEQUENCE: 56
gagcatcctg aaccgcaacg cgcccca                                              27

SEQ ID NO: 57           moltype = DNA   length = 27
FEATURE                 Location/Qualifiers
misc_feature            1..27
                        note = Primer impE1 164-A 2F
source                  1..27
                        mol_type = other DNA
                        organism = synthetic construct
SEQUENCE: 57
gagcatcctg aagcccaacg cgcccca                                              27

SEQ ID NO: 58           moltype = DNA   length = 27
FEATURE                 Location/Qualifiers
misc_feature            1..27
                        note = Primer impE1 164-V 2F
source                  1..27
```

```
                            mol_type = other DNA
                            organism = synthetic construct
SEQUENCE: 58
gagcatcctg aagtccaacg cgccca                                        27

SEQ ID NO: 59              moltype = DNA  length = 27
FEATURE                    Location/Qualifiers
misc_feature               1..27
                           note = Primer impE1 164-I 2F
source                     1..27
                           mol_type = other DNA
                           organism = synthetic construct
SEQUENCE: 59
gagcatcctg aaatccaacg cgccca                                        27

SEQ ID NO: 60              moltype = DNA  length = 27
FEATURE                    Location/Qualifiers
misc_feature               1..27
                           note = Primer impE1 164-L 2F
source                     1..27
                           mol_type = other DNA
                           organism = synthetic construct
SEQUENCE: 60
gagcatcctg aactgcaacg cgccca                                        27

SEQ ID NO: 61              moltype = DNA  length = 27
FEATURE                    Location/Qualifiers
misc_feature               1..27
                           note = Primer impE1 164-M 2F
source                     1..27
                           mol_type = other DNA
                           organism = synthetic construct
SEQUENCE: 61
gagcatcctg aaatgcaacg cgccca                                        27

SEQ ID NO: 62              moltype = DNA  length = 27
FEATURE                    Location/Qualifiers
misc_feature               1..27
                           note = Primer impE1 164-F 2F
source                     1..27
                           mol_type = other DNA
                           organism = synthetic construct
SEQUENCE: 62
gagcatcctg aattccaacg cgccca                                        27

SEQ ID NO: 63              moltype = DNA  length = 27
FEATURE                    Location/Qualifiers
misc_feature               1..27
                           note = Primer impE1 164-Y 2F
source                     1..27
                           mol_type = other DNA
                           organism = synthetic construct
SEQUENCE: 63
gagcatcctg aataccaacg cgccca                                        27

SEQ ID NO: 64              moltype = DNA  length = 27
FEATURE                    Location/Qualifiers
misc_feature               1..27
                           note = Primer impE1 164-W 2F
source                     1..27
                           mol_type = other DNA
                           organism = synthetic construct
SEQUENCE: 64
gagcatcctg aatggcaacg cgccca                                        27

SEQ ID NO: 65              moltype = DNA  length = 26
FEATURE                    Location/Qualifiers
misc_feature               1..26
                           note = Primer XbaI-impE2 2 1F
source                     1..26
                           mol_type = other DNA
                           organism = synthetic construct
SEQUENCE: 65
gggtctagat tgcatgctgt gcaaga                                        26

SEQ ID NO: 66              moltype = DNA  length = 27
FEATURE                    Location/Qualifiers
misc_feature               1..27
                           note = Primer impE2 2-R 1R
```

```
source                  1..27
                        mol_type = other DNA
                        organism = synthetic construct
SEQUENCE: 66
ggagttttta gcgcgcattc cagtcct                                          27

SEQ ID NO: 67           moltype = DNA   length = 27
FEATURE                 Location/Qualifiers
misc_feature            1..27
                        note = Primer impE2 2-H 1R
source                  1..27
                        mol_type = other DNA
                        organism = synthetic construct
SEQUENCE: 67
ggagttttta gcgtgcattc cagtcct                                          27

SEQ ID NO: 68           moltype = DNA   length = 27
FEATURE                 Location/Qualifiers
misc_feature            1..27
                        note = Primer impE2 2-K 1R
source                  1..27
                        mol_type = other DNA
                        organism = synthetic construct
SEQUENCE: 68
ggagttttta gccttcattc cagtcct                                          27

SEQ ID NO: 69           moltype = DNA   length = 27
FEATURE                 Location/Qualifiers
misc_feature            1..27
                        note = Primer impE2 2-D 1R
source                  1..27
                        mol_type = other DNA
                        organism = synthetic construct
SEQUENCE: 69
ggagttttta gcgtccattc cagtcct                                          27

SEQ ID NO: 70           moltype = DNA   length = 27
FEATURE                 Location/Qualifiers
misc_feature            1..27
                        note = Primer impE2 2-E 1R
source                  1..27
                        mol_type = other DNA
                        organism = synthetic construct
SEQUENCE: 70
ggagttttta gcttccattc cagtcct                                          27

SEQ ID NO: 71           moltype = DNA   length = 27
FEATURE                 Location/Qualifiers
misc_feature            1..27
                        note = Primer impE2 2-S 1R
source                  1..27
                        mol_type = other DNA
                        organism = synthetic construct
SEQUENCE: 71
ggagttttta gcggacattc cagtcct                                          27

SEQ ID NO: 72           moltype = DNA   length = 27
FEATURE                 Location/Qualifiers
misc_feature            1..27
                        note = Primer impE2 2-T 1R
source                  1..27
                        mol_type = other DNA
                        organism = synthetic construct
SEQUENCE: 72
ggagttttta gcggtcattc cagtcct                                          27

SEQ ID NO: 73           moltype = DNA   length = 27
FEATURE                 Location/Qualifiers
misc_feature            1..27
                        note = Primer impE2 2-N 1R
source                  1..27
                        mol_type = other DNA
                        organism = synthetic construct
SEQUENCE: 73
ggagttttta gcgttcattc cagtcct                                          27

SEQ ID NO: 74           moltype = DNA   length = 27
FEATURE                 Location/Qualifiers
misc_feature            1..27
```

```
                    note = Primer impE2 2-Q 1R
source              1..27
                    mol_type = other DNA
                    organism = synthetic construct
SEQUENCE: 74
ggagttttta gcctgcattc cagtcct                                       27

SEQ ID NO: 75       moltype = DNA  length = 27
FEATURE             Location/Qualifiers
misc_feature        1..27
                    note = Primer impE2 2-C 1R
source              1..27
                    mol_type = other DNA
                    organism = synthetic construct
SEQUENCE: 75
ggagttttta gcgcacattc cagtcct                                       27

SEQ ID NO: 76       moltype = DNA  length = 27
FEATURE             Location/Qualifiers
misc_feature        1..27
                    note = Primer impE2 2-G 1R
source              1..27
                    mol_type = other DNA
                    organism = synthetic construct
SEQUENCE: 76
ggagttttta gcgcccattc cagtcct                                       27

SEQ ID NO: 77       moltype = DNA  length = 27
FEATURE             Location/Qualifiers
misc_feature        1..27
                    note = Primer impE2 2-P 1R
source              1..27
                    mol_type = other DNA
                    organism = synthetic construct
SEQUENCE: 77
ggagttttta gctggcattc cagtcct                                       27

SEQ ID NO: 78       moltype = DNA  length = 27
FEATURE             Location/Qualifiers
misc_feature        1..27
                    note = Primer impE2 2-A 1R
source              1..27
                    mol_type = other DNA
                    organism = synthetic construct
SEQUENCE: 78
ggagttttta gcagccattc cagtcct                                       27

SEQ ID NO: 79       moltype = DNA  length = 27
FEATURE             Location/Qualifiers
misc_feature        1..27
                    note = Primer impE2 2-L 1R
source              1..27
                    mol_type = other DNA
                    organism = synthetic construct
SEQUENCE: 79
ggagttttta gccagcattc cagtcct                                       27

SEQ ID NO: 80       moltype = DNA  length = 27
FEATURE             Location/Qualifiers
misc_feature        1..27
                    note = Primer impE2 2-M 1R
source              1..27
                    mol_type = other DNA
                    organism = synthetic construct
SEQUENCE: 80
ggagttttta gccatcattc cagtcct                                       27

SEQ ID NO: 81       moltype = DNA  length = 27
FEATURE             Location/Qualifiers
misc_feature        1..27
                    note = Primer impE2 2-F 1R
source              1..27
                    mol_type = other DNA
                    organism = synthetic construct
SEQUENCE: 81
ggagttttta gcgaacattc cagtcct                                       27

SEQ ID NO: 82       moltype = DNA  length = 27
FEATURE             Location/Qualifiers
```

-continued

```
misc_feature            1..27
                        note = Primer impE2 2-Y 1R
source                  1..27
                        mol_type = other DNA
                        organism = synthetic construct
SEQUENCE: 82
ggagtttttta gcgtacattc cagtcct                                              27

SEQ ID NO: 83           moltype = DNA  length = 27
FEATURE                 Location/Qualifiers
misc_feature            1..27
                        note = Primer impE2 2-W 1R
source                  1..27
                        mol_type = other DNA
                        organism = synthetic construct
SEQUENCE: 83
ggagtttttta gcccacattc cagtcct                                              27

SEQ ID NO: 84           moltype = DNA  length = 26
FEATURE                 Location/Qualifiers
misc_feature            1..26
                        note = Primer XbaI-impE2 2 2R
source                  1..26
                        mol_type = other DNA
                        organism = synthetic construct
SEQUENCE: 84
gggtctagat tgctcgccca cgcgca                                                26

SEQ ID NO: 85           moltype = DNA  length = 27
FEATURE                 Location/Qualifiers
misc_feature            1..27
                        note = Primer impE2 2-R 2F
source                  1..27
                        mol_type = other DNA
                        organism = synthetic construct
SEQUENCE: 85
aggactggaa tgcgcgctaa aaactcc                                               27

SEQ ID NO: 86           moltype = DNA  length = 27
FEATURE                 Location/Qualifiers
misc_feature            1..27
                        note = Primer impE2 2-H 2F
source                  1..27
                        mol_type = other DNA
                        organism = synthetic construct
SEQUENCE: 86
aggactggaa tgcacgctaa aaactcc                                               27

SEQ ID NO: 87           moltype = DNA  length = 27
FEATURE                 Location/Qualifiers
misc_feature            1..27
                        note = Primer impE2 2-K 2F
source                  1..27
                        mol_type = other DNA
                        organism = synthetic construct
SEQUENCE: 87
aggactggaa tgaaggctaa aaactcc                                               27

SEQ ID NO: 88           moltype = DNA  length = 27
FEATURE                 Location/Qualifiers
misc_feature            1..27
                        note = Primer impE2 2-D 2F
source                  1..27
                        mol_type = other DNA
                        organism = synthetic construct
SEQUENCE: 88
aggactggaa tggacgctaa aaactcc                                               27

SEQ ID NO: 89           moltype = DNA  length = 27
FEATURE                 Location/Qualifiers
misc_feature            1..27
                        note = Primer impE2 2-E 2F
source                  1..27
                        mol_type = other DNA
                        organism = synthetic construct
SEQUENCE: 89
aggactggaa tggaagctaa aaactcc                                               27

SEQ ID NO: 90           moltype = DNA  length = 27
```

```
FEATURE                 Location/Qualifiers
misc_feature            1..27
                        note = Primer impE2 2-S 2F
source                  1..27
                        mol_type = other DNA
                        organism = synthetic construct
SEQUENCE: 90
aggactggaa tgtccgctaa aaactcc                                              27

SEQ ID NO: 91           moltype = DNA  length = 27
FEATURE                 Location/Qualifiers
misc_feature            1..27
                        note = Primer impE2 2-T 2F
source                  1..27
                        mol_type = other DNA
                        organism = synthetic construct
SEQUENCE: 91
aggactggaa tgaccgctaa aaactcc                                              27

SEQ ID NO: 92           moltype = DNA  length = 27
FEATURE                 Location/Qualifiers
misc_feature            1..27
                        note = Primer impE2 2-N 2F
source                  1..27
                        mol_type = other DNA
                        organism = synthetic construct
SEQUENCE: 92
aggactggaa tgaacgctaa aaactcc                                              27

SEQ ID NO: 93           moltype = DNA  length = 27
FEATURE                 Location/Qualifiers
misc_feature            1..27
                        note = Primer impE2 2-Q 2F
source                  1..27
                        mol_type = other DNA
                        organism = synthetic construct
SEQUENCE: 93
aggactggaa tgcaggctaa aaactcc                                              27

SEQ ID NO: 94           moltype = DNA  length = 27
FEATURE                 Location/Qualifiers
misc_feature            1..27
                        note = Primer impE2 2-C 2F
source                  1..27
                        mol_type = other DNA
                        organism = synthetic construct
SEQUENCE: 94
aggactggaa tgtgcgctaa aaactcc                                              27

SEQ ID NO: 95           moltype = DNA  length = 27
FEATURE                 Location/Qualifiers
misc_feature            1..27
                        note = Primer impE2 2-G 2F
source                  1..27
                        mol_type = other DNA
                        organism = synthetic construct
SEQUENCE: 95
aggactggaa tgggcgctaa aaactcc                                              27

SEQ ID NO: 96           moltype = DNA  length = 27
FEATURE                 Location/Qualifiers
misc_feature            1..27
                        note = Primer impE2 2-P 2F
source                  1..27
                        mol_type = other DNA
                        organism = synthetic construct
SEQUENCE: 96
aggactggaa tgccagctaa aaactcc                                              27

SEQ ID NO: 97           moltype = DNA  length = 27
FEATURE                 Location/Qualifiers
misc_feature            1..27
                        note = Primer impE2 2-A 2F
source                  1..27
                        mol_type = other DNA
                        organism = synthetic construct
SEQUENCE: 97
aggactggaa tggctgctaa aaactcc                                              27
```

```
SEQ ID NO: 98           moltype = DNA  length = 27
FEATURE                 Location/Qualifiers
misc_feature            1..27
                        note = Primer impE2 2-L 2F
source                  1..27
                        mol_type = other DNA
                        organism = synthetic construct
SEQUENCE: 98
aggactggaa tgctggctaa aaactcc                                            27

SEQ ID NO: 99           moltype = DNA  length = 27
FEATURE                 Location/Qualifiers
misc_feature            1..27
                        note = Primer impE2 2-M 2F
source                  1..27
                        mol_type = other DNA
                        organism = synthetic construct
SEQUENCE: 99
aggactggaa tgatggctaa aaactcc                                            27

SEQ ID NO: 100          moltype = DNA  length = 27
FEATURE                 Location/Qualifiers
misc_feature            1..27
                        note = Primer impE2 2-F 2F
source                  1..27
                        mol_type = other DNA
                        organism = synthetic construct
SEQUENCE: 100
aggactggaa tgttcgctaa aaactcc                                            27

SEQ ID NO: 101          moltype = DNA  length = 27
FEATURE                 Location/Qualifiers
misc_feature            1..27
                        note = Primer impE2 2-Y 2F
source                  1..27
                        mol_type = other DNA
                        organism = synthetic construct
SEQUENCE: 101
aggactggaa tgtacgctaa aaactcc                                            27

SEQ ID NO: 102          moltype = DNA  length = 27
FEATURE                 Location/Qualifiers
misc_feature            1..27
                        note = Primer impE2 2-W 2F
source                  1..27
                        mol_type = other DNA
                        organism = synthetic construct
SEQUENCE: 102
aggactggaa tgtgggctaa aaactcc                                            27

SEQ ID NO: 103          moltype = DNA  length = 30
FEATURE                 Location/Qualifiers
misc_feature            1..30
                        note = Primer XbaI-impE2 64 1F
source                  1..30
                        mol_type = other DNA
                        organism = synthetic construct
SEQUENCE: 103
gggtctagaa aagagcttaa ggcagctgct                                         30

SEQ ID NO: 104          moltype = DNA  length = 27
FEATURE                 Location/Qualifiers
misc_feature            1..27
                        note = Primer impE2 64-R 1R
source                  1..27
                        mol_type = other DNA
                        organism = synthetic construct
SEQUENCE: 104
gaaaatcatc tggcgcaaag agctcat                                            27

SEQ ID NO: 105          moltype = DNA  length = 27
FEATURE                 Location/Qualifiers
misc_feature            1..27
                        note = Primer impE2 64-H 1R
source                  1..27
                        mol_type = other DNA
                        organism = synthetic construct
SEQUENCE: 105
gaaaatcatc tggtgcaaag agctcat                                            27
```

-continued

```
SEQ ID NO: 106           moltype = DNA   length = 27
FEATURE                  Location/Qualifiers
misc_feature             1..27
                         note = Primer impE2 64-D 1R
source                   1..27
                         mol_type = other DNA
                         organism = synthetic construct
SEQUENCE: 106
gaaaatcatc tggtccaaag agctcat                                              27

SEQ ID NO: 107           moltype = DNA   length = 27
FEATURE                  Location/Qualifiers
misc_feature             1..27
                         note = Primer impE2 64-K 1R
source                   1..27
                         mol_type = other DNA
                         organism = synthetic construct
SEQUENCE: 107
gaaaatcatc tgcttcaaag agctcat                                              27

SEQ ID NO: 108           moltype = DNA   length = 27
FEATURE                  Location/Qualifiers
misc_feature             1..27
                         note = Primer impE2 64-S 1R
source                   1..27
                         mol_type = other DNA
                         organism = synthetic construct
SEQUENCE: 108
gaaaatcatc tgggacaaag agctcat                                              27

SEQ ID NO: 109           moltype = DNA   length = 27
FEATURE                  Location/Qualifiers
misc_feature             1..27
                         note = Primer impE2 64-T 1R
source                   1..27
                         mol_type = other DNA
                         organism = synthetic construct
SEQUENCE: 109
gaaaatcatc tgggtcaaag agctcat                                              27

SEQ ID NO: 110           moltype = DNA   length = 27
FEATURE                  Location/Qualifiers
misc_feature             1..27
                         note = Primer impE2 64-N 1R
source                   1..27
                         mol_type = other DNA
                         organism = synthetic construct
SEQUENCE: 110
gaaaatcatc tggttcaaag agctcat                                              27

SEQ ID NO: 111           moltype = DNA   length = 27
FEATURE                  Location/Qualifiers
misc_feature             1..27
                         note = Primer impE2 64-Q 1R
source                   1..27
                         mol_type = other DNA
                         organism = synthetic construct
SEQUENCE: 111
gaaaatcatc tgctgcaaag agctcat                                              27

SEQ ID NO: 112           moltype = DNA   length = 27
FEATURE                  Location/Qualifiers
misc_feature             1..27
                         note = Primer impE2 64-C 1R
source                   1..27
                         mol_type = other DNA
                         organism = synthetic construct
SEQUENCE: 112
gaaaatcatc tggcacaaag agctcat                                              27

SEQ ID NO: 113           moltype = DNA   length = 27
FEATURE                  Location/Qualifiers
misc_feature             1..27
                         note = Primer impE2 64-P 1R
source                   1..27
                         mol_type = other DNA
                         organism = synthetic construct
SEQUENCE: 113
```

```
gaaaatcatc tgtggcaaag agctcat                                           27

SEQ ID NO: 114         moltype = DNA   length = 27
FEATURE                Location/Qualifiers
misc_feature           1..27
                       note = Primer impE2 64-A 1R
source                 1..27
                       mol_type = other DNA
                       organism = synthetic construct
SEQUENCE: 114
gaaaatcatc tgagccaaag agctcat                                           27

SEQ ID NO: 115         moltype = DNA   length = 27
FEATURE                Location/Qualifiers
misc_feature           1..27
                       note = Primer impE2 64-V 1R
source                 1..27
                       mol_type = other DNA
                       organism = synthetic construct
SEQUENCE: 115
gaaaatcatc tggaccaaag agctcat                                           27

SEQ ID NO: 116         moltype = DNA   length = 27
FEATURE                Location/Qualifiers
misc_feature           1..27
                       note = Primer impE2 64-I 1R
source                 1..27
                       mol_type = other DNA
                       organism = synthetic construct
SEQUENCE: 116
gaaaatcatc tggatcaaag agctcat                                           27

SEQ ID NO: 117         moltype = DNA   length = 27
FEATURE                Location/Qualifiers
misc_feature           1..27
                       note = Primer impE2 64-L 1R
source                 1..27
                       mol_type = other DNA
                       organism = synthetic construct
SEQUENCE: 117
gaaaatcatc tgcagcaaag agctcat                                           27

SEQ ID NO: 118         moltype = DNA   length = 27
FEATURE                Location/Qualifiers
misc_feature           1..27
                       note = Primer impE2 64-M 1R
source                 1..27
                       mol_type = other DNA
                       organism = synthetic construct
SEQUENCE: 118
gaaaatcatc tgcatcaaag agctcat                                           27

SEQ ID NO: 119         moltype = DNA   length = 27
FEATURE                Location/Qualifiers
misc_feature           1..27
                       note = Primer impE2 64-F 1R
source                 1..27
                       mol_type = other DNA
                       organism = synthetic construct
SEQUENCE: 119
gaaaatcatc tggaacaaag agctcat                                           27

SEQ ID NO: 120         moltype = DNA   length = 27
FEATURE                Location/Qualifiers
misc_feature           1..27
                       note = Primer impE2 64-Y 1R
source                 1..27
                       mol_type = other DNA
                       organism = synthetic construct
SEQUENCE: 120
gaaaatcatc tggtacaaag agctcat                                           27

SEQ ID NO: 121         moltype = DNA   length = 27
FEATURE                Location/Qualifiers
misc_feature           1..27
                       note = Primer impE2 64-W 1R
source                 1..27
                       mol_type = other DNA
                       organism = synthetic construct
```

```
SEQUENCE: 121
gaaaatcatc tgccacaaag agctcat                                              27

SEQ ID NO: 122         moltype = DNA   length = 30
FEATURE                Location/Qualifiers
misc_feature           1..30
                       note = Primer XbaI-impE2 64 2R
source                 1..30
                       mol_type = other DNA
                       organism = synthetic construct
SEQUENCE: 122
gggtctagac ggtcaatgaa gtctcaacgg                                           30

SEQ ID NO: 123         moltype = DNA   length = 27
FEATURE                Location/Qualifiers
misc_feature           1..27
                       note = Primer impE2 64-R 2F
source                 1..27
                       mol_type = other DNA
                       organism = synthetic construct
SEQUENCE: 123
atgagctctt tgcgccagat gattttc                                              27

SEQ ID NO: 124         moltype = DNA   length = 27
FEATURE                Location/Qualifiers
misc_feature           1..27
                       note = Primer impE2 64-H 2F
source                 1..27
                       mol_type = other DNA
                       organism = synthetic construct
SEQUENCE: 124
atgagctctt tgcaccagat gattttc                                              27

SEQ ID NO: 125         moltype = DNA   length = 27
FEATURE                Location/Qualifiers
misc_feature           1..27
                       note = Primer impE2 64-D 2F
source                 1..27
                       mol_type = other DNA
                       organism = synthetic construct
SEQUENCE: 125
atgagctctt tggaccagat gattttc                                              27

SEQ ID NO: 126         moltype = DNA   length = 27
FEATURE                Location/Qualifiers
misc_feature           1..27
                       note = Primer impE2 64-K 2F
source                 1..27
                       mol_type = other DNA
                       organism = synthetic construct
SEQUENCE: 126
atgagctctt tgaagcagat gattttc                                              27

SEQ ID NO: 127         moltype = DNA   length = 27
FEATURE                Location/Qualifiers
misc_feature           1..27
                       note = Primer impE2 64-S 2F
source                 1..27
                       mol_type = other DNA
                       organism = synthetic construct
SEQUENCE: 127
atgagctctt tgtcccagat gattttc                                              27

SEQ ID NO: 128         moltype = DNA   length = 27
FEATURE                Location/Qualifiers
misc_feature           1..27
                       note = Primer impE2 64-T 2F
source                 1..27
                       mol_type = other DNA
                       organism = synthetic construct
SEQUENCE: 128
atgagctctt tgacccagat gattttc                                              27

SEQ ID NO: 129         moltype = DNA   length = 27
FEATURE                Location/Qualifiers
misc_feature           1..27
                       note = Primer impE2 64-N 2F
source                 1..27
                       mol_type = other DNA
```

```
                                   organism = synthetic construct
SEQUENCE: 129
atgagctctt tgaaccagat gattttc                                            27

SEQ ID NO: 130           moltype = DNA   length = 27
FEATURE                  Location/Qualifiers
misc_feature             1..27
                         note = Primer impE2 64-Q 2F
source                   1..27
                         mol_type = other DNA
                         organism = synthetic construct
SEQUENCE: 130
atgagctctt tgcagcagat gattttc                                            27

SEQ ID NO: 131           moltype = DNA   length = 27
FEATURE                  Location/Qualifiers
misc_feature             1..27
                         note = Primer impE2 64-C 2F
source                   1..27
                         mol_type = other DNA
                         organism = synthetic construct
SEQUENCE: 131
atgagctctt tgtgccagat gattttc                                            27

SEQ ID NO: 132           moltype = DNA   length = 27
FEATURE                  Location/Qualifiers
misc_feature             1..27
                         note = Primer impE2 64-P 2F
source                   1..27
                         mol_type = other DNA
                         organism = synthetic construct
SEQUENCE: 132
atgagctctt tgccacagat gattttc                                            27

SEQ ID NO: 133           moltype = DNA   length = 27
FEATURE                  Location/Qualifiers
misc_feature             1..27
                         note = Primer impE2 64-A 2F
source                   1..27
                         mol_type = other DNA
                         organism = synthetic construct
SEQUENCE: 133
atgagctctt tggctcagat gattttc                                            27

SEQ ID NO: 134           moltype = DNA   length = 27
FEATURE                  Location/Qualifiers
misc_feature             1..27
                         note = Primer impE2 64-V 2F
source                   1..27
                         mol_type = other DNA
                         organism = synthetic construct
SEQUENCE: 134
atgagctctt tggtccagat gattttc                                            27

SEQ ID NO: 135           moltype = DNA   length = 27
FEATURE                  Location/Qualifiers
misc_feature             1..27
                         note = Primer impE2 64-I 2F
source                   1..27
                         mol_type = other DNA
                         organism = synthetic construct
SEQUENCE: 135
atgagctctt tgatccagat gattttc                                            27

SEQ ID NO: 136           moltype = DNA   length = 27
FEATURE                  Location/Qualifiers
misc_feature             1..27
                         note = Primer impE2 64-L 2F
source                   1..27
                         mol_type = other DNA
                         organism = synthetic construct
SEQUENCE: 136
atgagctctt tgctgcagat gattttc                                            27

SEQ ID NO: 137           moltype = DNA   length = 27
FEATURE                  Location/Qualifiers
misc_feature             1..27
                         note = Primer impE2 64-M 2F
source                   1..27
```

```
SEQUENCE: 137
atgagctctt tgatgcagat gattttc                                            27

SEQ ID NO: 138           moltype = DNA  length = 27
FEATURE                  Location/Qualifiers
misc_feature             1..27
                         note = Primer impE2 64-F 2F
source                   1..27
                         mol_type = other DNA
                         organism = synthetic construct
SEQUENCE: 138
atgagctctt tgttccagat gattttc                                            27

SEQ ID NO: 139           moltype = DNA  length = 27
FEATURE                  Location/Qualifiers
misc_feature             1..27
                         note = Primer impE2 64-Y 2F
source                   1..27
                         mol_type = other DNA
                         organism = synthetic construct
SEQUENCE: 139
atgagctctt tgtaccagat gattttc                                            27

SEQ ID NO: 140           moltype = DNA  length = 27
FEATURE                  Location/Qualifiers
misc_feature             1..27
                         note = Primer impE2 64-W 2F
source                   1..27
                         mol_type = other DNA
                         organism = synthetic construct
SEQUENCE: 140
atgagctctt tgtggcagat gattttc                                            27

SEQ ID NO: 141           moltype = AA  length = 221
FEATURE                  Location/Qualifiers
REGION                   1..221
                         note = ImpE1-CJI0323
source                   1..221
                         mol_type = protein
                         organism = unidentified
SEQUENCE: 141
LHAVQEVNDN EEDSLPGSDL GLREQKRLAT KHRIEDAATR LVDESSFDKV TIEEICEAAG          60
ISRRTFFNYF STKESAVIGA SSEPLTEKQR NDFLNADASN LLQLMVEQIK QHLESSHQSQ         120
AIHDRRQRIF ADPDVAVRAM AFRKERSRET MELIAQRLRE HPEKQRAPEL DPETEAMLLS         180
GFIREATWMA ISRPDRDCAL PVGDRIYRAM ELVKNYTKGL E                            221

SEQ ID NO: 142           moltype = AA  length = 549
FEATURE                  Location/Qualifiers
REGION                   1..549
                         note = ImpE2-CJI0323
source                   1..549
                         mol_type = protein
                         organism = unidentified
SEQUENCE: 142
MIAKNSTPST AGHASAHTAE EFPVANAEMA TPSAIDPNHG KKTADNVGII FAALMLTMLM          60
SSLEQMIFGS ALPTIVGELG GVDQMSWVIS AFMVTMTIAM PLAGQLGDRM GRKWVYISGI         120
SIFVIGSTLG GFANGMGMLI TGRAIQGFGA GIMMISSQSI VAEVVSARER GKFMGIMGGV         180
FGVSSVLGPV LGGWFTDGPG WRWGLWINIP LGLLAIIVCA FVLKLRVGEQ GFKGFDWMGF         240
AAIAITTSTL ILLTTWGGSE YEWTSPTILS MAAVVIVGAL LTVFIESRAS QPLIPVQLFK         300
NRNMVLTTLA GTVLGLAMMG VLGYMPTYLQ MVHTLTPTEA GLMMIPMMVG MIGVSTGVGF         360
IIAKTGNYKY YPIAGLAITA FALWWMSQMT VETSLTGIGV RFLVFGVGLG FVMQVLVLIV         420
QNSFPVSQVG TATAANNFFR QIGSALGASI VGSMFIHNMQ NEMATRLPDA LASLGKEGAA         480
ISQQFQGADA ANSLTPHAVA ELPDVLRDAI LNSYNDGLTP VIGMMVPLAI VAMLILFPLR         540
QERLKETIE                                                                549

SEQ ID NO: 143           moltype = DNA  length = 669
FEATURE                  Location/Qualifiers
misc_feature             1..669
                         note = ImpE1 NT - CJI0323
source                   1..669
                         mol_type = other DNA
                         organism = unidentified
SEQUENCE: 143
ttgcatgctg tgcaagaagt taatgacaat gaagaagact ccctccctgg cagtgacctc         60
gggttaaggg agcagaagcg attggcaacc aagcatcgca tcgaagacgc cgcgacacgg        120
ttggttgatg aatcgagctt tgacaaagta acaattgaag aaatttgcga agccgccggg        180
atttcccgac gcacctttttt taattatttc agcacgaaag aaagcgccgt tattggcgcg      240
```

-continued

```
tcctcggaac cgttgacgga aaagcaacgc aatgacttct tgaatgctga cgccagcaat  300
ctcctgcagc tgatggttga gcagatcaaa caacacttgg agtcttctca ccagagtcaa  360
gcgattcacg accgtcgtca gcgaatcttt gcggatccgg atgtcgcggt acgtgcaatg  420
gcgtttcgca aggaacgctc acgggaaacc atggagctaa tcgctcaacg tcttcgggag  480
catcctgaaa acaacgcgc cccagaattg gatccgaaa cagaggcgat gctgctgagc  540
ggattcattc gcgaagccac ctggatggct atctcacgac ccgatcgtga ttgtgcactg  600
ccagtgggtg accgcatcta tcgcgcgatg gaattggtaa agaattacac gaaaggactg  660
gaatgatag                                                          669

SEQ ID NO: 144         moltype = DNA  length = 1650
FEATURE                Location/Qualifiers
misc_feature           1..1650
                       note = ImpE2 NT - CJI0323
source                 1..1650
                       mol_type = other DNA
                       organism = unidentified
SEQUENCE: 144
atgatagcta aaaactccac cccaagcacg gccggccacg ccagtgctca cactgcggaa  60
gaattcccag tggccaatgc tgaaatggca acgccttcag caatcgaccc aaaccacggt  120
aaaaagaccg cggataacgt cggcattatc ttcgctgcct tgatgctcac catgctgatg  180
agctcttttgg agcagatgat tttcggttcc gctctgccaa ccatcgtcgg cgagctcggc  240
ggcgtggacc agatgagctg ggtaatttca gcatttatgg tcaccatgac cattgctatg  300
ccactagccg gtcagctcgg tgaccgcatg ggccgcaagt gggtctacat ctcaggtatc  360
tccattttcg ttattggctc gacgctcggt ggctttgcca atggcatggg catgctgatc  420
accgacgtg caatccaggg cttcggtgcc ggcatcatga tgatttcctc gcagtcgatt  480
gtggctgagg ttgtctccgc acgtgagcgc ggcaagttca tggtattat gggcggcgaa  540
tttggcgtct cctccgtact gggtccagtt ctccggtggct ggttcaccga tggtcccggt  600
tggcgttggg gcctcgtggat caacattcca ctgggtctgc tggcaattat tgtctgcgct  660
ttcgtactga agctgcgcgt gggcgagcaa ggctttaagg gctttgactg gatgggtttt  720
gcggccatcg caatcacgac cagcaccctg attctgctca ccacttgggg cggaagcgaa  780
tacgagtgga cttccccaac tattttgtcc atggctgccg tagtcatcgt cggcgcgctg  840
ctcaccgtgt tcattgagtc gcgtgcatcc cagccgctga tccggttcaa gctatttaag  900
aaccgcaaca tggttttgac caccctcgcc ggtactgttt gggtctggc catgatgggc  960
gtgctcggct acatgccaac ctacctgcag atggtgcaca ccctgacgcc aactgaagca 1020
ggcttgatga tgatcccgat gatggtcggc atgatcggtg tctccactgg tgttggcttc 1080
atcatcgcta agaccggcaa ctacaagtac taccccatcg cgggcctggc catcacggcg 1140
tttgctttgt ggtggatgtc ccagatgacc gttgagactt cattgaccgg tatcggagtt 1200
cgcttccttg tattcggtgt cggcttgggc tttgtcatgc aggtactggt gctgattgtt 1260
caaaactcct tccctgtatc gcaggtcggt actgccacgg cttcttccgc 1320
cagattggtt cggcattggg tgcttccatc gtgggttcga tgttcattca aatatgcag 1380
aatgagatgg ctacccgttt gcctgatgcc cttgcatcgt tgggcaagga aggcgccgct 1440
atttcgcagc agttccaagg tgcagatgcc gccaactcct tgactccgca cgcagtcgca 1500
gagcttcccg atgtcctccg tgacgctatc ttaaattcct acaatgacgg tctgacccc 1560
gtgattggca tgatggtgcc actggccatt gttgcaatgc tgattttgtt cccactgcgc 1620
caagagcgct tgaaggaaac catcgaataa                                  1650

SEQ ID NO: 145         moltype = AA  length = 222
FEATURE                Location/Qualifiers
REGION                 1..222
                       note = ImpE1-164K
source                 1..222
                       mol_type = protein
                       organism = unidentified
SEQUENCE: 145
LHAVQEVNDN EEDSLPGSDL GLREQKRLAT KHRIEDAATR LVDESSFDKV TIEEICEAAG  60
ISRRTFFNYF STKESAVIGA SSEPLTEKQR NDFLNADASN LLQLMVEQIK QHLESSHQSQ 120
AIHDRRQRIF ADPDVAVRAM AFRKERSRET MELIAQRLRE HPEKQRAPEL DPETEAMLLS 180
GFIREATWMA ISRPDRDCAL PVGDRIYRAM ELVKNYTKGL EW                    222

SEQ ID NO: 146         moltype = DNA  length = 669
FEATURE                Location/Qualifiers
misc_feature           1..669
                       note = ImpE1 NT-164K
source                 1..669
                       mol_type = other DNA
                       organism = unidentified
SEQUENCE: 146
ttgcatgctg tgcaagaagt taatgacaat gaagaagact ccctccctgg cagtgacctc  60
gggttaaggg agcagaagcg attggcaacc aagcatcgca tcgaagacgc cgcgacacgg 120
ttggttgatg aatcgagctt tgacaaagta acaattgaag aaatttgcga agccgccggg 180
atttcccgac gcacctttt taattattc agcacgaaag aaagcgccgt tattggcgcg 240
tcctcggaac cgttgacgga aaagcaacgc aatgacttct tgaatgctga cgccagcaat 300
ctcctgcagc tgatggttga gcagatcaaa caacacttgg agtcttctca ccagagtcaa 360
gcgattcacg accgtcgtca gcgaatcttt gcggatccgg atgtcgcggt acgtgcaatg 420
gcgtttcgca aggaacgctc acgggaaacc atggagctaa tcgctcaacg tcttcgggag 480
catcctgaaa acaacgcgc cccagaattg gatccgaaa cagaggcgat gctgctgagc 540
ggattcattc gcgaagccac ctggatggct atctcacgac ccgatcgtga ttgtgcactg 600
ccagtgggtg accgcatcta tcgcgcgatg gaattggtaa agaattacac gaaaggactg 660
gaatggtag                                                          669
```

```
SEQ ID NO: 147          moltype = AA  length = 549
FEATURE                 Location/Qualifiers
REGION                  1..549
                        note = ImpE2 - V2I
source                  1..549
                        mol_type = protein
                        organism = unidentified
SEQUENCE: 147
MIAKNSTPST AGHASAHTAE EFPVANAEMA TPSAIDPNHG KKTADNVGII FAALMLTMLM    60
SSLGQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                          549

SEQ ID NO: 148          moltype = DNA  length = 1650
FEATURE                 Location/Qualifiers
misc_feature            1..1650
                        note = ImpE2 NT - V2I
source                  1..1650
                        mol_type = other DNA
                        organism = unidentified
SEQUENCE: 148
atgatagcta aaaactccac cccaagcacg gccggccacg ccagtgctca cactgcggaa    60
gaattcccag tggccaatgc tgaaatggca acgccttcga caatcgaccc aaaccacggt   120
aaaaagaccg cggataacgt cggcattatc ttcgctgcct tgatgctcac catgctgatg   180
agctctttgg gcagatgat  tttcggttcc gctctgccaa ccatcgtcgg cgagctcggc   240
ggcgtggacc agatgagctg ggtaatttca gcatttatgg tcaccatgac cattgctatg   300
ccactagccg gtcagctcgg tgaccgcatg ggccgcaagt gggtctacat ctcaggtatc   360
tccattttcg ttattggctc gacgctcggt ggctttgcca atggcatgga catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctgcgcgt gggcgagcaa ggctttaagg gctttgactg gatgggtttt   720
gcggccatcg caatcacgac cagcaccctg attctgctca ccacttgggg cggaagcgaa   780
tacgagtgga cttccccaac tattttgtcc atggctgccg tagtcatcgt cggcgcgctg   840
ctcaccgtgt tcattgagtc gcgtgcatcc cagccgctga tcccggttca gctatttaag   900
aaccgcaaca tggttttgac caccctcgcc ggtactgtt  tgggtctggc catgatgggc   960
gtgctcggct acatgccaac ctacctgcag atggtgcaca ccctgacgcc aactgaagca  1020
ggcttgatga tgatcccgat gatggtcggc atgatcggtg tctccactgg tgttggcttc  1080
atcatcgcta agaccggcaa ctacaagtac tacccatcg  gggcctggc catcacggcg  1140
tttgctttgt ggtggatgtc ccagatgacc gttgagactt cattgaccgg tatcggagtt  1200
cgcttccttg tattcggtgt cggcttgggc tttgtcatgc aggtactggt gctgattgtt  1260
caaaactcct ccctgtatc  gcaggtcggt actgccacgg cggctaataa cttcttccgc  1320
cagattggtt cggcattggg tgcttccatc gtgggttcga tgttcattca caatatgcag  1380
aatgagatgg ctacccgttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgaccccc  1560
gtgattggca tgatggtgcc actggccatt gttgcaatgc tgattttgtt cccactcgcg  1620
caagagcgct tgaaggaaac catcgaataa                                   1650

SEQ ID NO: 149          moltype = AA  length = 549
FEATURE                 Location/Qualifiers
REGION                  1..549
                        note = ImpE2 - G64E
source                  1..549
                        mol_type = protein
                        organism = unidentified
SEQUENCE: 149
MVAKNSTPST AGHASAHTAE EFPVANAEMA TPSAIDPNHG KKTADNVGII FAALMLTMLM    60
SSLEQMIFGS ALPTIVGELG GVDQMSWVIS AFMVTMTIAM PLAGQLGDRM GRKWVYISGI   120
SIFVIGSTLG GFANGMGMLI TGRAIQGFGA GIMMISSQSI VAEVVSARER GKFMGIMGGV   180
FGVSSVLGPV LGGWFTDGPG WRWGLWINIP LGLLAIIVCA FVLKLRVGEQ GFKGFDWMGF   240
AAIAITTSTL ILLTTWGGSE YEWTSPTILS MAAVVIVGAL LTVFIESRAS QPLIPVQLFK   300
NRNMVLTTLA GTVLGLAMMG VLGYMPTYLQ MVHTLTPTEA GLMMIPMMVG MIGVSTGVGF   360
IIAKTGNYKY YPIAGLAITA FALWWMSQMT VETSLTGIGV RFLVFGVGLG FVMQVLVLIV   420
QNSFPVSQVG TATAANNFFR QIGSALGASI VGSMFIHNMQ NEMATRLPDA LASLGKEGAA   480
ISQQFQGADA ANSLTPHAVA ELPDVLRDAI LNSYNDGLTP VIGMMVPLAI VAMLILFPLR   540
QERLKETIE                                                          549

SEQ ID NO: 150          moltype = DNA  length = 1650
FEATURE                 Location/Qualifiers
misc_feature            1..1650
```

```
                    note           = ImpE2 NT - G64E
source              1..1650
                    mol_type       = other DNA
                    organism       = unidentified
SEQUENCE: 150
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg agcagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttttg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tggtattat gggcggcgtc     540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt gggtctggc catgatgggc      960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
atcatcgcta agaccggcaa ctacaagtac taccccatcg cgggcctggc catcaccgcg   1140
tttgctttgt ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtgggttcga tgttcattca caatatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgacccc    1560
gtgattggca tgatggtgcc actggccatt gttgcaatgc tgattttgtt cccactgcgc   1620
caagagcgct tgaaggaaac catcgaataa                                      1650

SEQ ID NO: 151     moltype = AA   length = 549
FEATURE            Location/Qualifiers
REGION             1..549
                    note           = ImpE2 - G64D
source              1..549
                    mol_type       = protein
                    organism       = unidentified
SEQUENCE: 151
MVAKNSTPST AGHASAHTAE EFPVANAEMA TPSAIDPNHG KKTADNVGII FAALMLTMLM     60
SSLDQMIFGS ALPTIVGELG GVDQMSWVIS AFMVTMTIAM PLAGQLGDRM GRKWVYISGI    120
SIFVIGSTLG GFANGMGMLI TGRAIQGFGA GIMMISSQSI VAEVVSARER GKFMGIMGGV    180
FGVSSVLGPV LGGWFTDGPG WRWGLWINIP LGLLAIIVCA FVLKLRVGEQ GFKGFDWMGF    240
AAIAITTSTL ILLTTWGGSE YEWTSPTILS MAAVVIVGAL LTVFIESRAS QPLIPVQLFK    300
NRNMVLTTLA GTVLGLAMMG VLGYMPTYLQ MVHTLTPTEA GLMMIPMMVG MIGVSTGVGF    360
IIAKTGNYKY YPIAGLAITA FALWWMSQMT VETSLTGIGV RFLVFGVGLG FVMQVLVLIV    420
QNSFPVSQVG TATAANNFFR QIGSALGASI VGSMFIHNMQ NEMATRLPDA LASLGKEGAA    480
ISQQFQGADA ANSLTPHAVA ELPDVLRDAI LNSYNDGLTP VIGMMVPLAI VAMLILFPLR    540
QERLKETIE                                                              549

SEQ ID NO: 152     moltype = DNA   length = 1650
FEATURE            Location/Qualifiers
misc_feature       1..1650
                    note           = ImpE2 NT - G64D
source              1..1650
                    mol_type       = other DNA
                    organism       = unidentified
SEQUENCE: 152
atggtagcta aaaactccac cccaagcacg gccggccacg ccagtgctca cactgcggaa     60
gaattcccag tggccaatgc tgaaatggca acgccttcag caatcgaccc aaaccacggt    120
aaaaagaccg cggataacgt cggcattatc ttcgctgcct tgatgctcac catgctgatg    180
agctctttgg accagatgat tttcggttcc gctctgccaa ccatcgtcgg cgagctcggc    240
ggcgtggacc agatgagctg ggtaatttca gcatttatgg tcaccatgac cattgctatg    300
ccactagccg gtcagctcgg tgaccgcatg ggccgcaagt gggtctacat ctcaggtatc    360
tccatttttg ttattggctc gacgctcggt ggctttgcca atggcatggg catgctgatc    420
accggacgtg caatccaggg cttcggtgcc ggcatcatga tgatttcctc gcagtcgatt    480
gtggctgagg ttgtctccgc acgtgagcgc ggcaagttca tggtattat gggcggcgtc     540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt    720
gcggccatcg caatcacgac cagcaccctg attctgctca ccacttgggg cggaagcgaa    780
tacgagtgga cttccccaac tattttgtcc atggctgccg tagtcatcgt cggcgcgctg    840
ctcaccgtgt tcattgagtc gcgtgcatcc cagccgctga tcccggttca gctatttaag    900
aaccgcaaca tggttttgac caccctcgcc ggtactgttt gggtctggc catgatgggc      960
gtgctcggct acatgccaac ctacctgcag atggtgcaca ccctgacgcc aactgaagca   1020
ggcttgatga tgatcccgat gatggtcggc atgatcggtg tctccactgg tgttggcttc   1080
```

```
atcatcgcta agaccggcaa ctacaagtac taccccatcg cgggcctggc catcacggcg   1140
tttgctttgt ggtggatgtc ccagatgacc gttgagactt cattgaccgg tatcggagtt   1200
cgcttccttg tattcggtgt cggcttgggc tttgtcatgc aggtactggt gctgattgtt   1260
caaaactcct tccctgtatc gcaggtcggt actgccacgg cggctaataa cttcttccgc   1320
cagattggtt cggcattggg tgcttccatc gtggggttcga tgttcattca caatatgcag   1380
aatgagatgg ctacccgttt gcctgatgcc cttgcatcgt tgggcaagga aggcgccgct   1440
atttcgcagc agttccaagg tgcagatgcc gccaactcct tgactccgca cgcagtcgca   1500
gagcttcccg atgtcctccg tgacgctatc ttaaattcct acaatgacgg tctgaccccc   1560
gtgattggca tgatggtgcc actggccatt gttgcaatgc tgattttgtt cccactcgcg   1620
caagagcgct tgaaggaaac catcgaataa                                    1650

SEQ ID NO: 153          moltype = DNA  length = 1650
FEATURE                 Location/Qualifiers
misc_feature            1..1650
                        note = ImpE2 NT - V2I G64E
source                  1..1650
                        mol_type = other DNA
                        organism = unidentified
SEQUENCE: 153
atgatagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg agcagatgat tttcggttcc gctctgccaa ccatcgtcgg cgagctcggc   240
ggcgtggacc agatgagctg ggtaatttca gcatttatgg tcaccatgac cattgctatg   300
ccactagccg gtcagctcgg tgaccgcatg gccgcaagt gggtctacat ctcaggtatc   360
tccatttttcg ttattggctc gacgctcggt ggctttgcca atggcagtgg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctgcgcgt gggcgagcaa ggctttaagg gctttgactg gatgggtttt   720
gcggccatcg caatcacgac cagcaccctg attctgctca ccactggggg cggaagcgaa   780
tacgagtgga cttccccaac tattttgtcc atggctgccg tagtcatcgt cggcgcgctg   840
ctcaccgtgt tcattgagtc gcgtgcatcc cagccgctga tccgggttca gctatttaag   900
aaccgcaaca tggttttgac caccctcgcc ggtactgttt tgggtctggc catgatgggc   960
gtgctcggct acatgccaac ctacctgcag atggtgcaca ccctgacgcc aactgaagca  1020
ggcttgatga tgatcccgat gatggtcggc atgatcggtg tctccactgg tgttggcttc  1080
atcatcgcta agaccggcaa ctacaagtac taccccatcg cgggcctggc catcacggcg  1140
tttgctttgt ggtggatgtc ccagatgacc gttgagactt cattgaccgg tatcggagtt  1200
cgcttccttg tattcggtgt cggcttgggc tttgtcatgc aggtactggt gctgattgtt  1260
caaaactcct tccctgtatc gcaggtcggt actgccacgg cggctaataa cttcttccgc  1320
cagattggtt cggcattggg tgcttccatc gtggggttcga tgttcattca caatatgcag  1380
aatgagatgg ctacccgttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgaccccc  1560
gtgattggca tgatggtgcc actggccatt gttgcaatgc tgattttgtt cccactcgcg  1620
caagagcgct tgaaggaaac catcgaataa                                   1650

SEQ ID NO: 154          moltype = DNA  length = 2312
FEATURE                 Location/Qualifiers
misc_feature            1..2312
                        note = ImpE NT - CJI0323
source                  1..2312
                        mol_type = other DNA
                        organism = unidentified
SEQUENCE: 154
ttgcatgctg tgcaagaagt taatgacaat gaagaagact ccctccctgg cagtgacctc    60
gggttaaggg agcagaagcg attggcaacc aagcatcgca tcgaagacgc cgcgacacgg   120
ttggttgatg aatcgagctt tgacaaagta acaattgaag aaatttgcga agccgccggg   180
atttcccgac gcaccttttt taattatttc agcacgaaag aaagcgccgt tattggcgcg   240
tcctcggaac cgttgacgga aaagcaacgc aatgactct gaatgctga cgccagcaat   300
ctcctgcagc tgatggttga gcagatcaaa caacacttgg agtcttctca ccagagtcaa   360
gcgattcacg accgtcgtca gcgaatcttt gcggatccgg atgtcgcggt acgtgcaatg   420
gcgtttcgca aggaacgctc acgggaaacc atggagctaa tcgctcaacg tcttcggagg   480
catcctgaaa acaacgcgcc cccagaattg gatccggaaa cagaggcgat gctgctgagc   540
ggattcattc gcaagccac ctggatggct atctcacgac ccgatcgtga ttgtgcactg   600
ccagtggggt accgcatcta tcgcgcgatg gaattggtaa agaattacac gaaaggactg   660
gaatgatagc taaaaactcc accccaagca cggccggcca cgccagtgct cacactgcgg   720
aagaattccc agtggccaat gctgaaatgg caacgccttc agcaatcgac ccaaaccacg   780
gtaaaaagac cgcggataac gtcggcatta tcttcgctgc cttgatgctc accatgctga   840
tgagctcttt ggagcagatg attttcggtt ccgctctgcc aaccatcgtc ggcgagctcg   900
gcggcgtgga ccagatgagc tgggtaattt cagcatttat ggtcaccatg accattgcta   960
tgccactagc cggtcagctc ggtgaccgca tggccgcaa gtgggtctac atctcaggta  1020
tctccatttt cgttattggc tcgacgctcg gtggctttgc caatggcagt ggcatgctga  1080
tcaccggacg tgcaatccag ggcttcggtg ccggcatcat gatgatttcc tcgcagtcga  1140
ttgtggctga ggttgtctcc gcacgtgagc gcggcaagtt catgggtatt atgggcggcg  1200
tctttggcgt ctcctccgta ctgggtccag ttctcggtgg ctggttcacc gatggtcccg  1260
gttggcgttg gggcctgtgg atcaacattc cactgggtct gctggcaatt attgtctgcg  1320
ctttcgtact gaagctgcgc gtgggcgagc aaggctttaa gggctttgac tggatgggtt  1380
```

```
ttgcggccat cgcaatcacg accagcaccc tgattctgct caccacttgg ggcggaagcg 1440
aatacgagtg gacttcccca actattttgt ccatggctgc cgtagtcatc gtcggcgcgc 1500
tgctcaccgt gttcattgag tcgcgtgcat cccagccgct gatcccggtt cagctattta 1560
agaaccgcaa catggttttg accaccctcg ccggtactgt tttgggtctg gccatgatgg 1620
gcgtgctcgg ctacatgcca acctacctgc agatggtgca caccctgacg ccaactgaag 1680
caggcttgat gatgatcccg atgatggtcg gcatgatcgg tgtctccact ggtgttggct 1740
tcatcatcgc taagaccggc aactacaagt actacccat cgcgggcctg gccatcacgg 1800
cgtttgcttt gtggtggatg tcccagatga ccgttgagac ttcattgacc ggtatcggag 1860
ttcgcttcct tgtattcggt gtcggcttgg gctttgtcat gcaggtactg gtgctgattg 1920
ttcaaaactc cttccctgta tcgcaggtcg gtactgccac ggcggctaat aacttcttcc 1980
gccagattgg ttcggcattg ggtgcttcca tcgtgggttc gatgttcatt cacaatatgc 2040
agaatgagat ggctacccgt ttgcctgatg cccttgcatc gttgggcaag gaaggcgccg 2100
ctatttcgca gcagttccaa ggtgcagatg ccgccaactc cttgactccg cacgcagtcg 2160
cagagcttcc cgatgtcctc cgtgacgcta tcttaaattc ctacaatgac ggtctgaccc 2220
ccgtgattgg catgatggtg ccactggcca ttgttgcaat gctgattttg ttcccactgc 2280
gccaagagcg cttgaaggaa accatcgaat aa                               2312
```